United States Patent [19]
Lynnworth et al.

[11] Patent Number: 5,962,790
[45] Date of Patent: Oct. 5, 1999

[54] ULTRASONIC PATH BUNDLE AND SYSTEMS

[75] Inventors: Lawrence C. Lynnworth, Waltham; Yi Liu, Bolton, both of Mass.

[73] Assignee: Panametrics, Inc., Del.

[21] Appl. No.: 08/878,456

[22] Filed: Jun. 18, 1997

Related U.S. Application Data

[63] Continuation of application No. 08/477,761, Jun. 7, 1995, abandoned.

[51] Int. Cl.$^6$ .................................................. G01N 29/28
[52] U.S. Cl. ................................... 73/644; 73/861.18
[58] Field of Search ............................. 73/644, 642, 629, 73/861.18

[56] References Cited

U.S. PATENT DOCUMENTS

| 3,584,327 | 6/1971 | Murry | 15/104.16 |
| 3,825,887 | 7/1974 | Murry | 367/191 |
| 4,297,607 | 10/1981 | Lynnworth et al. | 73/642 |
| 4,337,843 | 7/1982 | Wendel | 73/644 |
| 5,159,838 | 11/1992 | Lynnworth | 073/644 |

FOREIGN PATENT DOCUMENTS

| 1253247 | 4/1989 | Canada . |
| WO 93/16381 | 8/1993 | WIPO . |

OTHER PUBLICATIONS

Gelles, I.L. (1966) "Optical–Fiber Ultrasonic Delay Lines" *Journal of the Acoustical Society of America* 39(6):1111–1119;
Rider, R.S. (1970) "Environmental Testing of Flexible Jacketed Fiber Optic Bundles" *S.P.I.E. Seminar Proceedings*21:43–48.
Madaras, E.I. (1995) "Device for Ultrasonic Scanning of Curved Object" NASA Tech Briefs Feb. 1995:50;.
E.J. Murry, "A Unique System for Transmission of Ultrasonic Energy Over Fibrous Bundles," *Ultrasonics*, Jul. 1970, pp. 168–173.

*Primary Examiner*—John E. Chapman
*Attorney, Agent, or Firm*—Nutter, McClennen & Fish, LLP

[57] ABSTRACT

An encapsulated or rigid bundle of rods forms a substantially non-dispersive buffer usable in extreme environments, operable over wide bandwidth, and in some implementations, easily repairable in the field. In one preferred configuration, suitable for measuring the flow of low-molecular-weight gases over a wide range of pressure, temperature and flow rates, the bundle is made of about one thousand stainless steel welding rods tightly packed inside a 1-inch diameter tube. The rigid encapsulated assembly is sealed at the end that is in contact with the gas and may be sealed into a high-pressure flange in a manner that yields broadband transmission characteristics. A second buffer bundle, aligned with the first bundle, may be pressure-coupled on the other side of the flange. Ultrasonic pulses transmitted into the first bundle remote from the gas are transmitted with little loss and little pulse distortion into the gas, while the transducer is thermally isolated by the second bundle and remains near ambient temperature. The high-pressure flange is thinned locally over a central area yet supports the rod safely and withstands pressures of 300 bar. This locally-thin region supports and aligns both buffers, while transmitting a broad band-width pulse in the preferred axial direction, while discouraging transmission in all other directions. This helps reduce solid-body-borne crosstalk and results in a high signal-to-noise ratio and high accuracy in the measurement of flow or other measurands. Signals may be combined to remove noise and then be processed to compute flow-related terms. The bundles are non-degrading waveguides to carry signals through degrading environments. This is useful for numerous stack, freestream and chordal path configurations, as well as clamp-on systems and special mode-converting configurations. Beam shaping and steering may be passively effected with patterned bundle constructions.

18 Claims, 18 Drawing Sheets

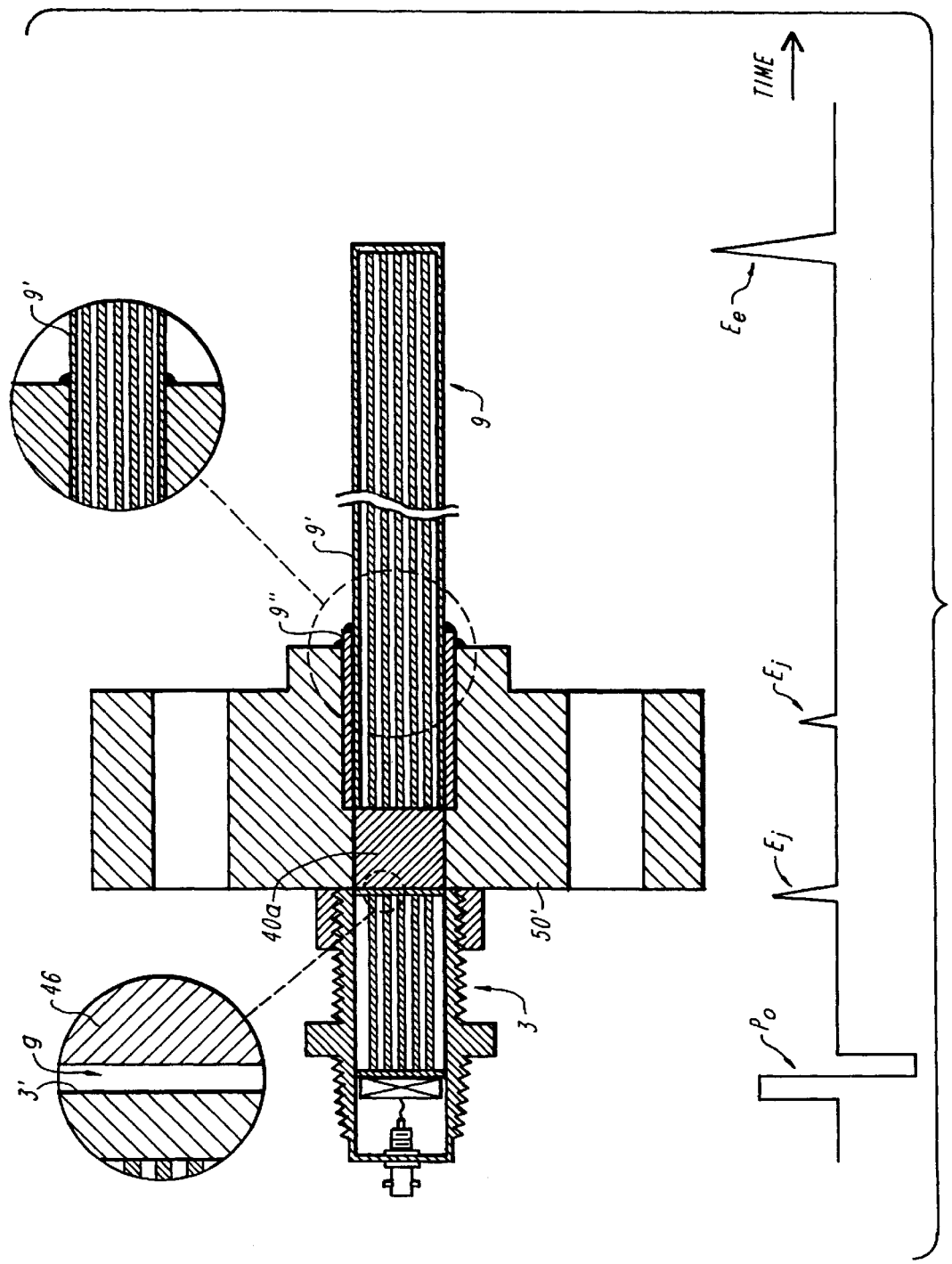

FIG. 9B
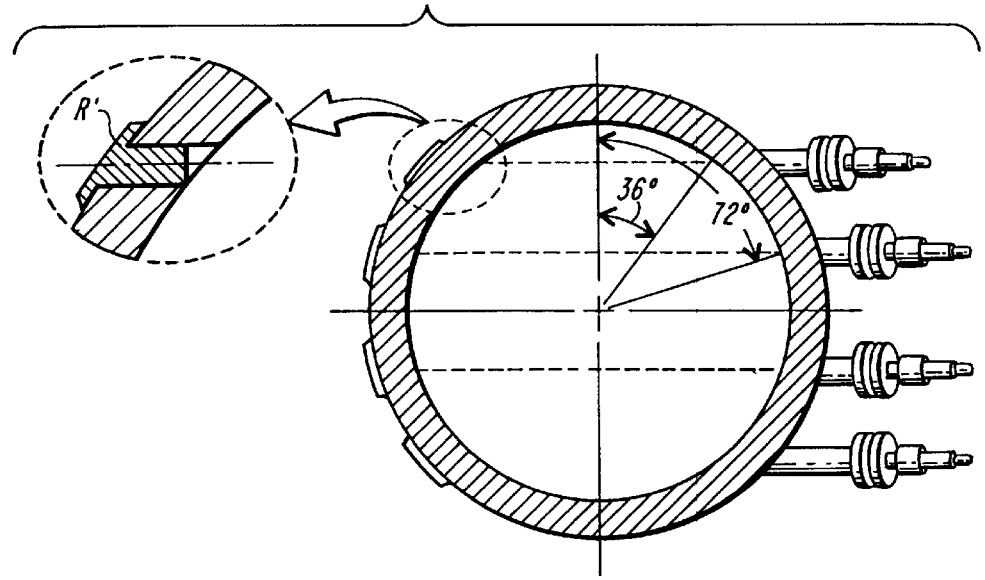
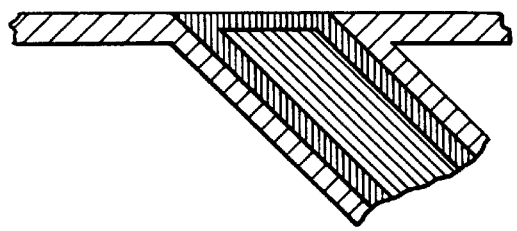
FIG. 9D
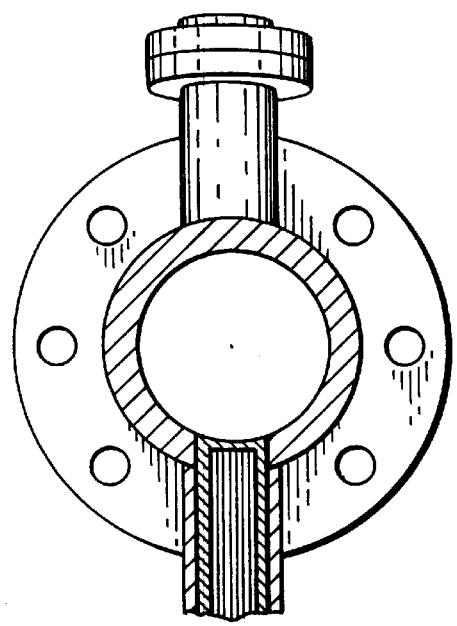
FIG. 9E
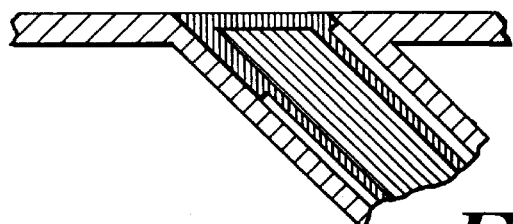
FIG. 9F

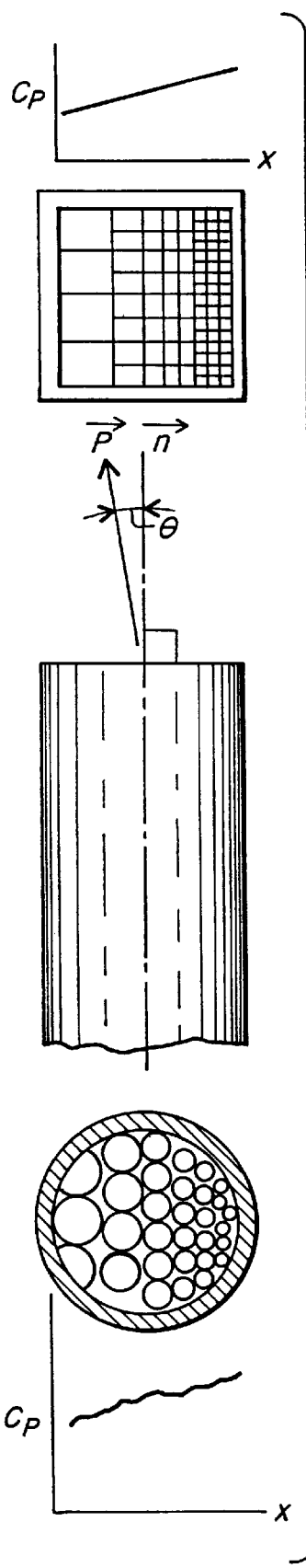
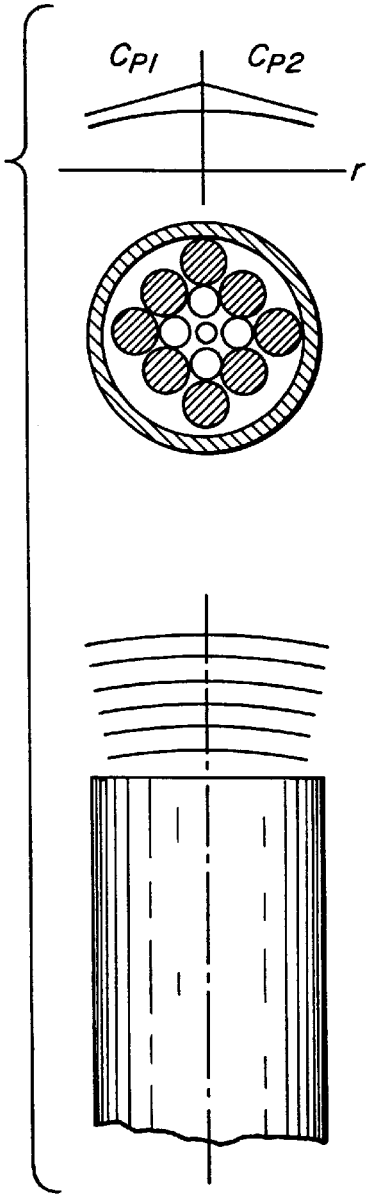
FIG. 11B
FIG. 11C

ULTRASONIC PATH BUNDLE AND SYSTEMS

This application is a continuation of application Ser. No. 08/477,761 filed on Jun. 7, 1995 Entitled: Ultrasonic Path Bundle and Systems now abandoned.

BACKGROUND OF THE INVENTION

The present invention relates to ultrasonics, and more particularly to all or portions of an ultrasonic system which includes coupling signals between transducer and an object or body of material through which those signals are to propagate. Particular applications may involve coupling into a gas at high temperature where some form of isolation, such as a buffer rod, is required.

Buffer rods have been used in ultrasonics for over fifty years to separate a transducer crystal from media under investigation that are at very high temperature. This is analogous to tending a red-hot fire with a long steel poker so as to not burn one's hands.

In ultrasonic measurements, it is important that the buffer not corrupt the signals of interest. Accordingly, much effort over the years has gone into avoiding the sidewall echoes generated by mode conversion. Such mode conversion occurs when longitudinal waves strike the wall near grazing incidence, generating shear waves, which in turn reflect multiple times diagonally across the rod. Each reflection generates a delayed replica of the original longitudinal pulse. Probably the most commonly-used way to avoid sidewall echoes is to thread the buffer. This method is often adequate, but has the disadvantage that it is quite lossy. For example, a solid steel buffer rod of 25 mm diameter and length of about 30 cm experiences a beam spread loss of about 20 dB, for a 500 kHz signal, assuming the longitudinal wave starts as a plane wave across the entire diameter of the rod.

Other known methods for preventing beam spread or diffraction loss in solid buffer rods include (i) the use of shear waves rather than longitudinal waves, as described in U.S. Pat. No. 3,477,278 of L. Lynnworth, and (ii) the use of a buffer rod in which the outer portion has a higher sound speed than the core, as described in U.S. Pat. No. 5,241,287 of Jen.

Furthermore, if hollow buffers are considered, one can avoid most of the diffraction loss and also avoid sidewall echoes. But in certain applications, it is not easy to correctly eliminate errors due to uncertainties in the time of travel down a hollow tube, in which the sound-conducting fluid may have a temperature or compositional gradient. Hollow tubes also run the risk of becoming filled with residues or condensate, which loads the walls and significantly alters their propagation properties. Also, at high flow velocities they resonate and create strong acoustic interferences.

In 1966, I. L. Gelles described non-dispersive operation of individual or bundled glass fibers to form flexible ultrasonic delay lines. These bundles, formed of fiber optic cable encased in a loose plastic sheath, had their fibers all fused or joined together by epoxy to form a practical termination. However, Gelles found high attenuation even in a very short distance of propagation through the bonded region, reporting an attenuation of "roughly greater than 10 dB/mm of coated-fiber length." (I. L. Gelles, Optical-Fiber Ultrasonic Delay Lines, *J. Acoust. Soc. Am.*, 39 (6), pp. 1111–1119 (1966)). With this construction, Gelles was able to adjust the bond thickness to work better for a particular frequency or to minimize an undesired or spurious pulse, and he suggested that that construction would have usefulness for pick-off points, re-entrant delay lines and particular devices such as fiber-based acoustic modulators. However, to applicant's knowledge, the acoustical use of optical fibers has not found application to transmission link or buffer constructions in the subsequent decades.

Thus, there remain problems in delivering or recovering well-defined acoustic signals when the process or measurement environment requires that the transducer be spatially remote. These problems may be particularly daunting when the process involves a gas at high temperature and high pressure, so that multiple considerations of physical isolation or containment, signal strength, and acoustic path impedance discontinuities all affect performance. For example, the seemingly simple requirement of measuring gas flow velocity accurately within ±1% over a wide flow range, for a low molecular weight gas, starting near or at atmospheric pressure and building up to 200 bar continuous, and for gas temperatures ranging up to 200° C. in normal operation and 450° C. in upset conditions, actually imposes a long list of requirements on the ultrasonic measuring system.

A practical system must accommodate considerations of cost, flexibility, signal isolation, and useful frequency range, as well as factors relating to calibration, maintainability and compatibility with existing equipment.

Accordingly, it would be desirable to provide an improved ultrasonic system.

SUMMARY OF THE INVENTION

In accordance with the present invention, a rigid link formed of stiff substantially non-dispersive rods is provided in an ultrasonic signal path. In one embodiment, the link is a buffer which acts as a signal-preserving and physically extending stand-off to isolate a transducer or coupling from destructive thermal, chemical or other physical conditions. Two or more such links may connect in series to carry signals between a transducer and an ultimate measurement or signal point. In a preferred embodiment, the rods are joined together in a solid sheet or disc at one end, which may be machined to a particular thickness or otherwise worked to augment or to enhance definition and coupling of the signal of interest. In a preferred embodiment of this aspect of the invention, the termination is a portion of a flange or cover plate forming a readily installed pressure-hardy closure for a process line or vessel. Each of the rods has a defined length so that they couple to transmit a combined signal or receive a detected signal coherently.

In other aspects or embodiments, the disc may include a $\lambda/4$ matching layer for a specific frequency, and the link may operate in systems employing signals that are odd integral multiples of that frequency, or harmonically-related frequencies. In still other embodiments, the ends of a bundle may be terminated by coupling at different points along a surface to convert between compressional wave energy in the rods and flexural wave energy of the surface. The surface may for example be the wall of a cylinder acting as a high-frequency sound source or receiver, wherein the flexural excitation of the cylinder provides an impedance-matched coupling of the signal with a surrounding gas. The signal path link of the present invention propagates a given frequency at one phase velocity but may propagate different frequencies with different speeds. One system utilizing this property involves Fourier synthesis of special impulse waveforms built up from tone bursts of two or more different frequencies launched at different times from one end of the link. A single channel system utilizes such a link to provide a signal of enhanced edge definition. A pattern of different diameter rods in a bundle focuses or steers the beam, while shaping of the output face controls beam direction. A processing system may couple pairs of elements to cancel noise.

BRIEF DESCRIPTION OF DRAWINGS

These and other features of the invention will be understood by a person versed in the art, from the description and claims presented herein, taken together with illustrative embodiments and explanatory drawings, wherein:

FIGS. 4A–4D illustrate a preferred construction of a link end portion;

FIGS. 9A–9F illustrate a number of directed bundle embodiments;

DETAILED DESCRIPTION

Figure 1A:
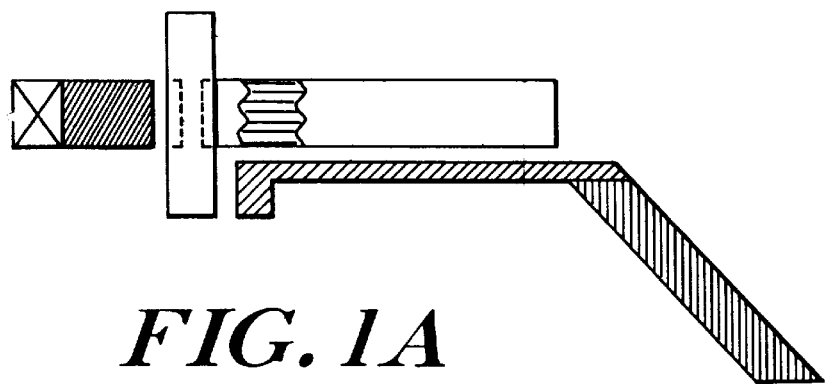
FIG. 1A shows a system utilizing an ultrasonic path link in accordance with the present invention.

FIG. 1A shows basic elements of a system 10 in accordance with the present invention, wherein a transducer 11 is used to perform one or both of the operations of launching ultrasonic signals into, and receiving ultrasonic signals from a measurement medium 20 such as liquid or gas, which is generally held within a containment structure 25. Structure 25, if present, may be a pipe, stack or other conduit, a tank or a process vessel. An acoustic path extends between the relevant portion of the measurement medium 20 and the transducer 11, and is defined along at least part of its length by a link element 13. Link 13 carries the acoustic signal along a non-measurement leg of its path, i.e., a portion of its path that is not directly affected by the property of the fluid being measured. Thus, for example, link 13 may couple the transducer 1 to or through the wall of the containment structure, or may carry the signal from some coupling point to a position closer to the free stream of the medium 20 within structure 25.

By way of example, medium 20 may be a low-molecular weight hydrocarbon or gas in a process line of a plant conduit operating at a temperature of 100–200° C. and at an elevated pressure of 100–200 bar. In this case, the transducer 11 must be effectively coupled through a massive steel containment wall and must further be sufficiently physically isolated from the hot measurement environment to prevent thermal degradation of the transducer. The link 13 thus serves as a buffer to allow coupling of the transducer.

Figure 1:
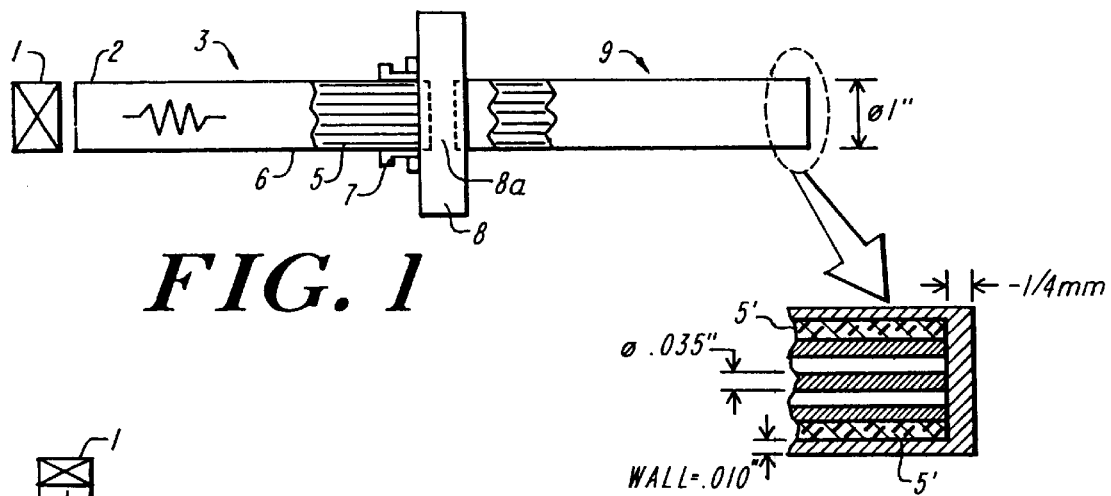
FIG. 1 shows a first embodiment of the invention.

In a basic embodiment, link 13 is formed by assembling a plurality of small diameter rods, such as a steel piano wire, into a bundle which forms a rigid path element that can be fastened to the wall and carry the signal without dispersion. FIG. 1 illustrates the invention in such a system.

Referring to FIG. 1, and proceeding generally from left to right, a piezoelectric crystal 1 is epoxied to the left end 2 of a first bundle buffer 3 according to the present invention, which is a bundle of segments of thin steel rods. An ultrasonic pulse 4 launched by the crystal is shown schematically. It travels down the rods that comprise the bundle at a phase velocity $$c_{ext} = \sqrt{(E/\rho)} \; [1-(\pi\sigma a/\lambda)^2]$$

where $\alpha$ is the rod diameter, and $\pi$ is the Poission's ratio of the rod material.

One such rod is denoted 5. Each rod serves as a waveguide, and according to this invention, the set of rods are assembled to preserve the individual properties of each rod, but have them act coherently. That is, the rods are not significantly coupled to each other along their lengths, but are joined at a common end into a well-defined structure. The above equation implies that if the rods are small enough compared to wavelength $\lambda$, $c_{ext}$ is very nearly equal to the square root of the Young's modulus E divided by density $\rho$. For stainless steel rods, this phase velocity is 5000 m/s near room temperature and decreases by about 10% at 500° C.

In the illustrated construction, the rods 5 may be stuffed into a sleeve 6 of the same material, which may have a sleeve wall thickness selected such that the lowest-order symmetrical Lamb wave ($S_o$ mode) transmits compressional waves in the sleeve at essentially the same speed as do the rods. One would expect that the tighter the rods would be packed, the more the boundary conditions would change on individual rods and on the sleeve, and that this would alter the propagation properties adversely. However, we have found that one may tightly pack the rods into the sleeve, without incurring dispersion. Applicant conjectures that the elements behave as if they were unbounded, because contacts between adjacent elements, and between outer elements and the surrounding sleeve, are of very small area compared to the surface area of the element or sleeve, occurring only at points (mathematically speaking), even though, in fact, the elements are squeezed into the sleeve 6. By matching the phase velocities in sleeve and waveguide elements, one may minimize dispersion in the bundle buffer. To reduce coupling from the waveguides (e.g., rods) to the sleeve, one can further arrange by choice of material, frequency and thickness or rod diameters that the relative soundspeed $c_{sleeve} \geq c_{rods}$.

The sleeve and its contents so assembled are called a sleeved bundle. The rods, though tightly packed, might still slide in or out along the axial direction. This bundle is next turned into a fixed or rigid assembly. The rods are restrained axially by fixing one end of the rods together, e.g., electron beam welding all the tips together for a distance on the order of one millimeter. The fused ends are also EB welded to the tube to seal the welded end, which can then be machined off square, flat and very smooth. This procedure may be done at both ends, to result in a totally encapsulated bundle that is evacuated (because the EB welding is necessarily performed under vacuum), and the sleeved and sealed bundle can then be handled almost as if it were a solid bar of stainless steel, although acoustically, it presents a non-dispersive propagation characteristic of the thin rods which fill its interior. Note that stainless steel or other metals, while having a particular longitudinal velocity of about 6000 meters/second, have extensional velocities of about 5000 meters/second or less, depending on rod diameter or wall thickness compared to wavelength.

The sleeve may generally have a thickness in the range of 0.010 to 0.100 inches or greater. Applicant has found the sleeve thickness to have relatively little effect on bundle performance, so its thickness may be selected to enhance other performance aspects such as environmental hardiness, or ease of welding or assembly.

As further shown in FIG. 1, a threaded member 7 is welded around the sleeve, allowing the first buffer bundle 3 to be threaded into pressure contact with the smooth surface of a recess in flange 8. By way of example, this flange may be taken to have the diameter and thickness dimensions of a standard 1.5-inch, 2500 psi rated, raised face flange. A second recess is shown on the opposite or "process" side of the flange, leaving a thin continuous web 8a in the center. The second recess also provides a stabilizing cavity for holding a second signal line buffer 9. While the flange for 300 bar gas service must be, for example, 50 mm thick at its raised face cross section, i.e., at its circumferential bolt-down ring, it can be thinned to about 7.5 mm, only 15% of the full thickness over a central region of diameter 25.4 mm and still not yield under pressure. Advantageously, the second buffer or signal path link 9 is nickel-brazed at its "flange" end to the bottom of the recess or cavity. The second buffer, in the present example, may be encapsulated much like bundle 3, but its length may be different for reasons having to do with the gas temperature $T_{gas}$ compared to the Curie temperature $\theta_c$ of the piezoelectric crystal 1, and temperature-compensation for delays in the buffers. The second buffer could be pressure coupled, with a threaded nut like nut 7 of the first one, but welding is preferable to avoid the possibility of accidental loosening of the element which is to be located internally in the process environment.

This is because the second buffer is not accessible during normal process operations, so it could not be retightened until the plant is shut down for maintenance. By brazing, followed by welding around the periphery, a permanent coupling is assured for buffer 9. By the same token, the first buffer 3 could also be permanently coupled, but that would preclude easy repair or replacement at some later date if one wished to replace the first buffer with another having a better crystal or a crystal of a different frequency, to suit different process gases or different process conditions.

Advantageously, by making the first and second buffers of unequal lengths, the echo train introduced by bundle ends can be employed to yield information on the transit time in each segment of the path, which is useful when performing system diagnostics. For example, the echo train can disclose asymmetries in the process, or the coupling efficiency at bundle junctions, or bundle temperature.

For buffers constructed as above, and for ultrasonic frequencies $f$<500 kHz, a suitable diameter for the rods is $2\alpha$=0.035 inches, or 0.9 mm. This is the smallest readily-available diameter for SS316 welding rods. The cusps between elements in a tightly-packed array of such rods may be partly filled by still smaller rods. Around the outermost ring of rods, inserting smaller fill rods will reduce the unsupported circumferential span of the sleeve and will increase the pressure rating that the sleeve can withstand without yielding or collapse. Coating with a ceramic paste may also be employed to fill the outermost cusps, but the ceramic coating would generally not have the same sound speed as the SS rods and sleeve and so is not as favorable a solution. We have found that an outer sleeve thickness of ¼ mm (0.020 inches) is suitable for test pressures up to 300 bar when the sleeve is packed full of rods of 0.9 mm diameter.

A useful length for such a bundle buffer, corresponding to the initial lengths that the rods of the first and second buffers are cut, is on the order of 30 cm (one foot). Measurements on such prototypes show that lengths up to one meter or longer are practical, insofar as attenuation and pulse distortion are concerned. A 25.4-mm diameter bundle that is one meter long, has a length to diameter ratio 1000/25.4=39.37 or approximately 40:1. The construction principles described here are applicable to even longer bundles and/or slenderer ones, where the length to diameter ratio can be 100:1 or even greater.

It is interesting to recall that to accommodate welding and radiographic or other inspection procedures, prior art nozzles often have lengths in the range of 15 to 30 cm, or 6 to 12 inches. The buffers described herein are suitable for use inside such nozzles, and such signal-guiding is advantageous even when the process gas is not at high temperature. For example, the process fluid can be methane at high pressure, but at a temperature between −20° C. to +60° C., or it can be steam, which is typically at high temperature and high pressure. In some vent stacks, both pressure and temperature are near ambient, yet it would still be advantageous to employ such a bundle to conduct the ultrasound from the flange end of a nozzle right up to the freestream.

By encapsulating the bundle, corrosion, particulates and other potentially-fouling attributes of the process fluid are prevented from contaminating the waveguide system and causing eventual decalibration. The bundle thus serves as a non-degrading acoustic path link through a degrading environment.

For a gas at standard conditions (STP=0° C., 760 mm Hg pressure) a low molecular weight implies a low density, which in turn means low acoustic impedance Z, where Z=ρc. In the described systems, the bundle buffer transmits into and out of a medium whose impedance Z is orders of magnitude lower than that of the buffer. Note that the Z of hydrogen gas at STP is $10^{-4}$ compared to that of water.

Figure 3:
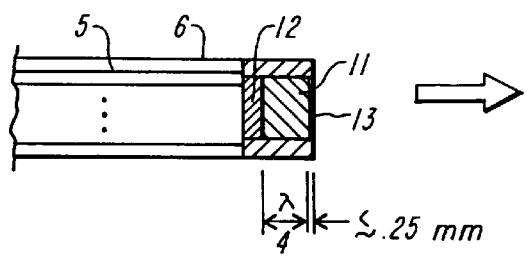
FIG. 3 shows a section through an end portion of the link of FIG. 1.

To accommodate such extremes of acoustic impedance along the propagation path, applicant introduces a quarter-wave impedance matcher at the radiating end of the buffer, as shown in FIG. 3. A small cavity is machined in the bundle end, into which a nickel-plated graphite disk 11 is fitted and further encapsulated by brazing and welding to provide such a matcher. Depending on the temperature of the braze, and disk dimensions, an intermediate layer of material 12, such as molybdenum, having a coefficient of thermal expansion between those of graphite and stainless steel may be included to prevent thermal fracture of the nickel or bonded-on graphite when brazing. The outermost boundary 13, which is formed of electroformed nickel or bonded-on 316 SS (stainless steel) in this example, is preferably thin compared to wavelength, e.g., is one quarter mm or less for use at frequencies between 100 and 500 kHz. The matching layer is preferably dimensioned one quarter wavelength thick at $f$=100 kHz, so that it is three quarter-wavelengths for a 300 kHz signal and five quarter-wavelengths thick for a 500 kHz signal. This assures that energy couples efficiently at three odd multiple frequencies $f$, $3f$, $5f$. For use only at frequencies $3f$, $5f$, a thinner quarter-wave matcher may be used. For applications at ordinary temperatures, the matching layer need not be refractory; it can be a syntactic foam, for example, and the bonding can be affected by epoxy instead of brazing. Similarly, for use at intermediate temperatures, a solder may be employed. When brazing in order to avoid cracking of the low-density graphite impedance matcher, the disc may be assembled in two-parts—for example a number of pie-segments, or a small diameter graphite disc surrounded by a concentric annular ring. For matching to a gas or light fluid, the plate is formed of a highly porous and very light material, which is preferably sealed to cover the pores and prevent fouling.

It would be desirable to operate the ultrasonic system over a wide range of flows and attenuations which occur as molecular weight of the medium varies, and more importantly as pressure, temperature and flow-induced noise and turbulence vary. Such operation is achieved in one embodiment by utilizing a crystal with a first, e.g., thickness resonance near 500 kHz and a second, e.g., radial resonance near 100 kHz, and which otherwise fits the geometrical constraints imposed by process piping and standard nozzles. One suitable compromise approaching these criteria is a PZT (lead zirconate titanate) crystal of thickness about 4 mm (0.160 inches) and diameter about 16 mm (⅝ inch). By selecting the bundle rods and sleeve wall to be thin enough to pass 500 kHz without significant dispersion, the lower 100 kHz signal will also pass without dispersion. By constructing the bundle for broad bandwidth in this manner, one may expect good propagation of coded signals, or may use the buffer in pulse-echo mode, for example, to interrogate hot steel for defects or for thickness measurements. Another construction to achieve broad bandwidth operation is to attach several crystals to the end of the bundle, each resonant at a particular frequency. They may all connected electrically in parallel, and they can be excited simultaneously by a spike excitation, or they can be swept in chirp or stepped chirp fashion.

When so adapted for multi-frequency operation, the bundle may be used adaptively in a system wherein the control sends and receives signals at each frequency and determines the quality of received signal at each frequency (e.g., the degree of attenuation, or the degradation of signal waveform), and then selects the highest frequency which has an acceptable signal transmission quality, for performing subsequent interrogations. This adaptive or feedback frequency selector thus allows the highest practical resolution to be obtained under the prevailing fluid conditions.

The buffer rods are substantially free of spurious echoes in the region between what may be called cardinal or principal echoes from the ends of the buffer, i.e., are free of echoes other than end echoes, allowing the buffer to be used in diverse applications, including pulse-echo applications, from delay lines to electrokinetic sonic amplitude (ESA). (ESA is discussed in NIST Special Publication 856, Subhas G. Malghan, ed., Electroacoustics for Characterization of Particulates and Suspensions, *Proceedings of Workshop held at the National Institute of Standards and Technology, Gaithersburg, Md.* (Feb. 3–4, 1993)). An example of a flow-related pulse-echo configuration for fluid is shown in FIG. 10E.

Certain combinations of construction, slightly different from those described above, may have advantages in particular circumstances. For example, the ends may be brazed but not welded. Pressure coupling can be enhanced by using certain coupling agents, thereby allowing one to relax somewhat the tolerances on flatness of the mating surfaces compared to what would be required if pressure alone is used for the end coupling the bundles in the acoustic path. Suitable coupling agents include anti-seize compounds containing nickel particles; soft nickel foil; gold-plated aluminum; gold-plated anodized aluminum; electroless or electroformed nickel on the ends of the buffer; and gold foil. Further examples of coupling agents appear in the ultrasonic coupling literature.

If an EB welding machine is unavailable or if the bundle length exceeds the capacity of the EB welder, an oxyacetylene torch may be used to fuse the ends and seal to the sleeve. TIG (tungsten inert gas) welding may also be used to fuse the ends and, in the flange 8, to radially build up the web 8*a* in a design wherein the flange initially has a hole through its center, into which the bundle is installed and welded. Fused silica, previously reported for use in high-temperature buffers for plasma measurements by Carnevale et al. in 1962, may be torch-fused by a skilled glassblower. The waveguide elements do not have to be made of a material identical to the sleeve, but the thermal coefficients of expansion are preferably reasonably well matched, if operation over a wide temperature range is contemplated.

Figure 5:
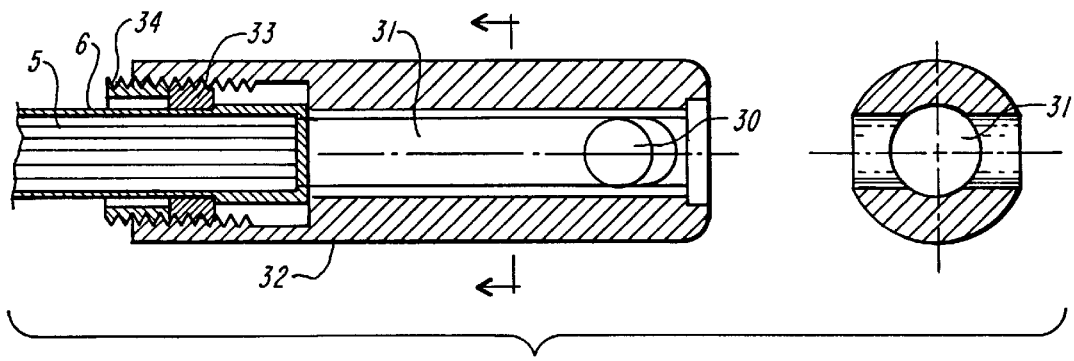
FIG. 5 shows an embodiment with right angle reflector.
Figure 5A:
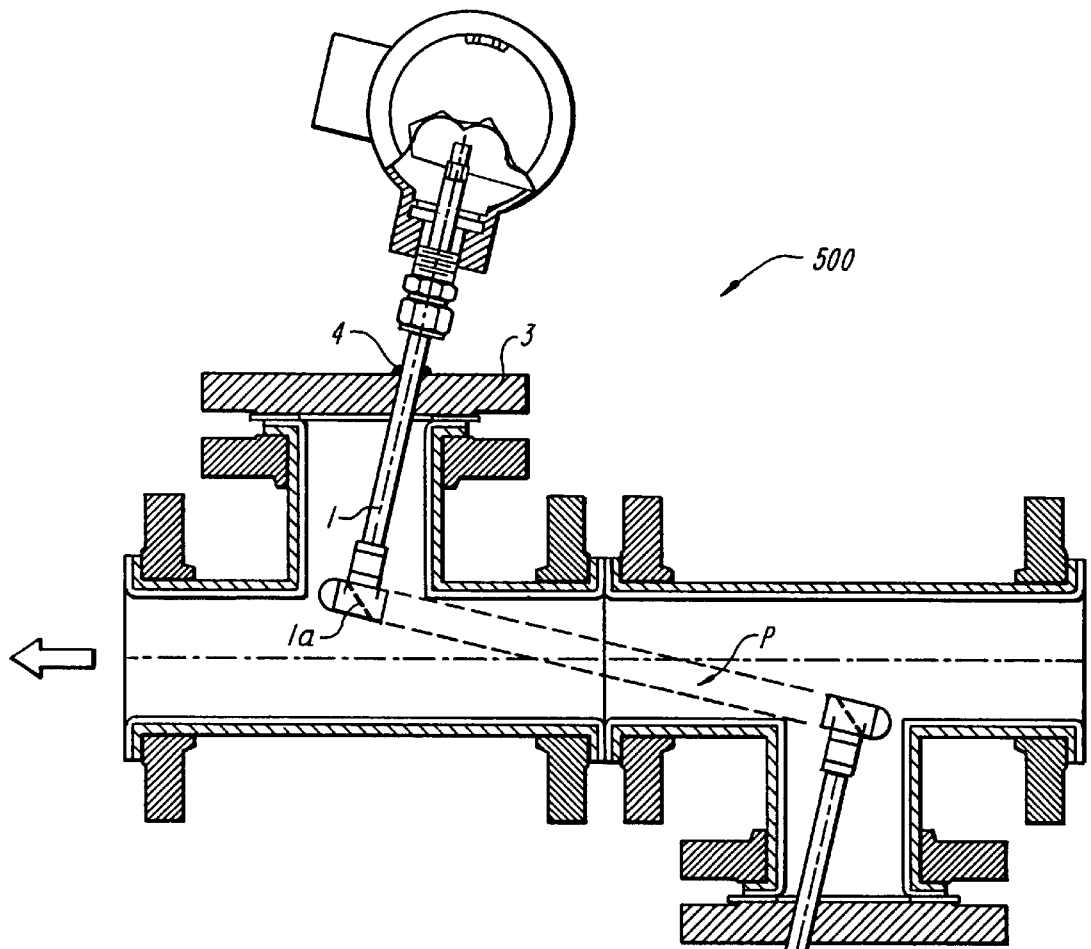
FIGS. 5A and 5B illustrates a system utilizing the embodiment of FIG. 5 and a detail thereof.
Figure 5B:
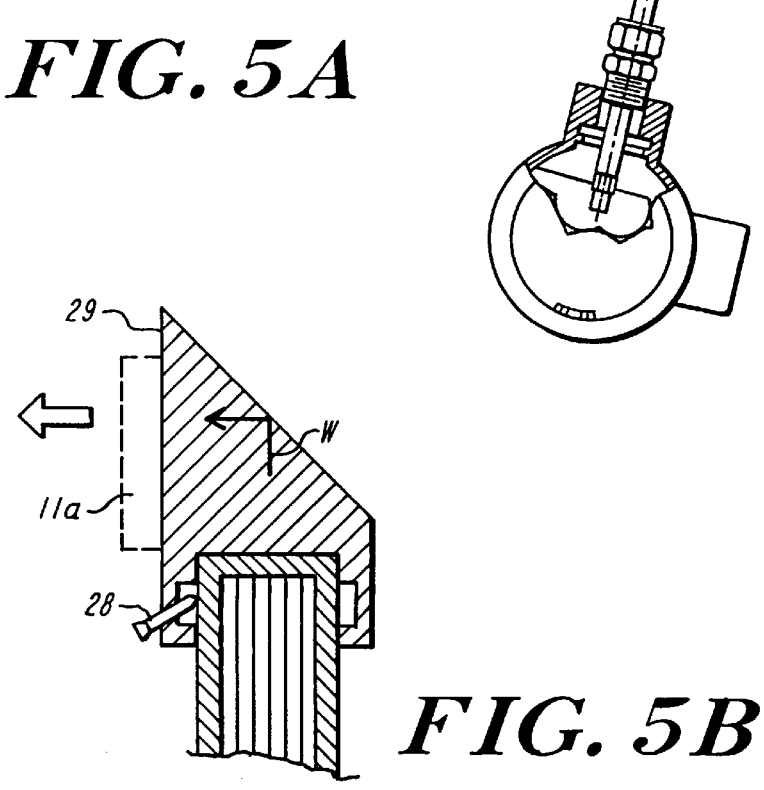

In flare gas applications, the "bias 90" configuration described in Smalling et al. in Proc. 39th Annual Symposium on Instrumentation for the Process Industry (1984) can be approximated by adding 45° reflectors 30 to the ends of the buffers, leaving gaps or a slot 31 so the gas can self-purge and self clean the radiating tip and reflector. Such an embodiment is shown in FIG. 5. Here the bundle effectively moves the signal source close to the reflector. The 45° reflector may also be coupled or bonded directly to the bundle end as shown in FIG. 5B.

Figure 6:
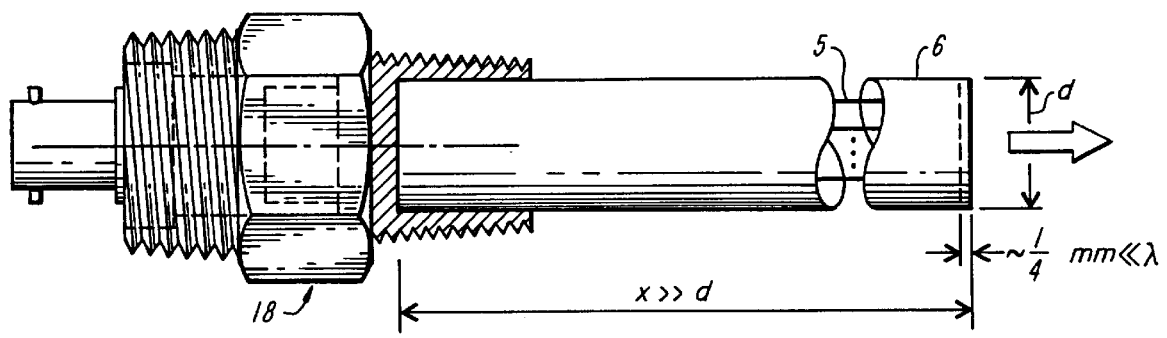
FIG. 6 shows another embodiment.

The bundle may also be installed in a pipe plug instead of in a flange. Such an embodiment is illustrated in FIG. 6.

Figure 7:
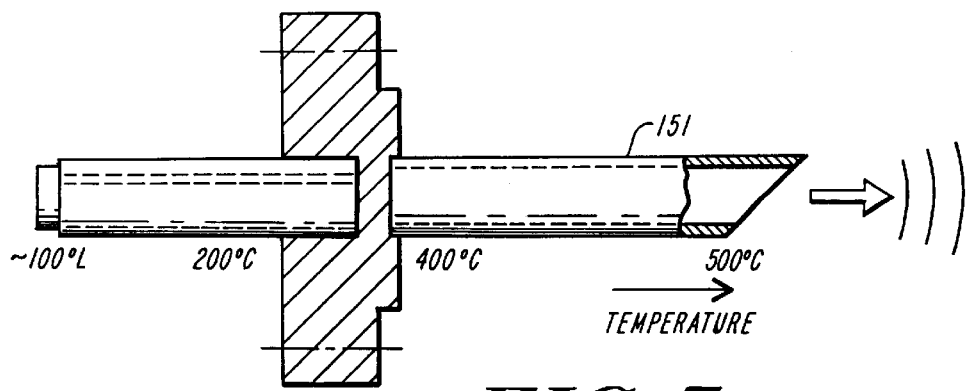
FIG. 7 show a two-link embodiment.

In an other embodiment, the bundle is outside the pressure boundary, and a simple hollow tube 15, forms the inner buffer, as shown in FIG. 7. These constructions and combinations illustrate the versatility of the bundle construction according to the present invention.

In early constructions of such a rigidized bundle buffer, applicant has found that it is difficult to form a homogenous fused end by simple electron beam welding as the material in the central region becomes irregular and cannot readily be machined flat. This problem has been overcome by TIG welding, where a wire provides weld material to build-up a continuous surface, while providing an effective and continuous weld at the rod end.

Figure 4A:
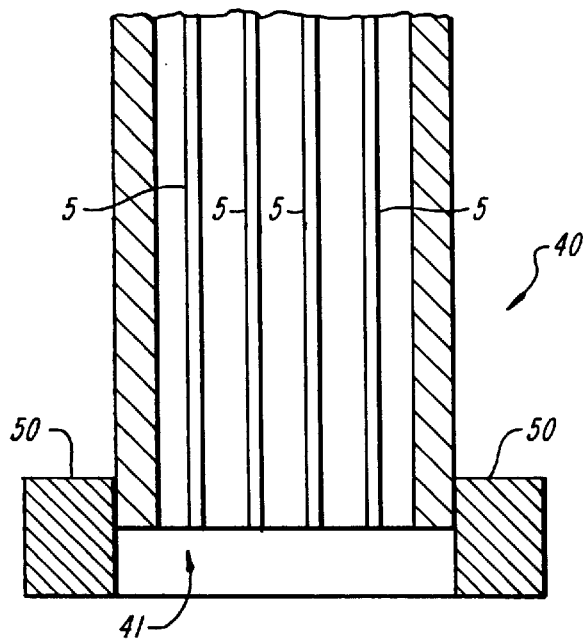
Figure 4B:
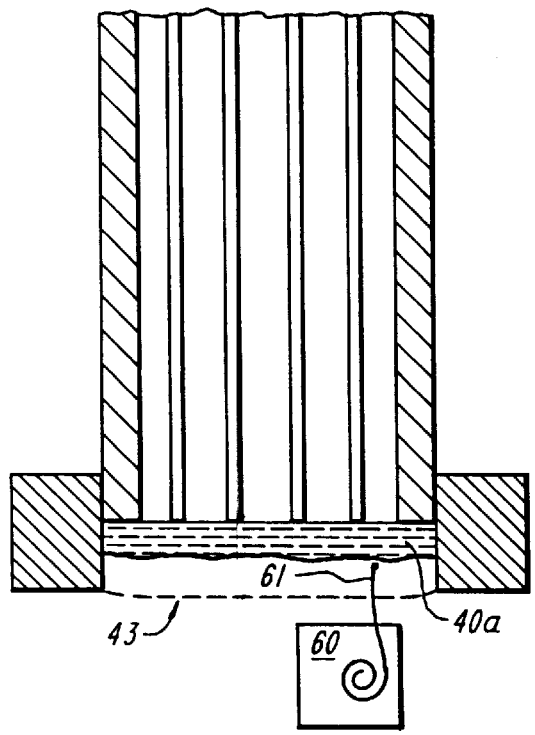
Figure 4C:
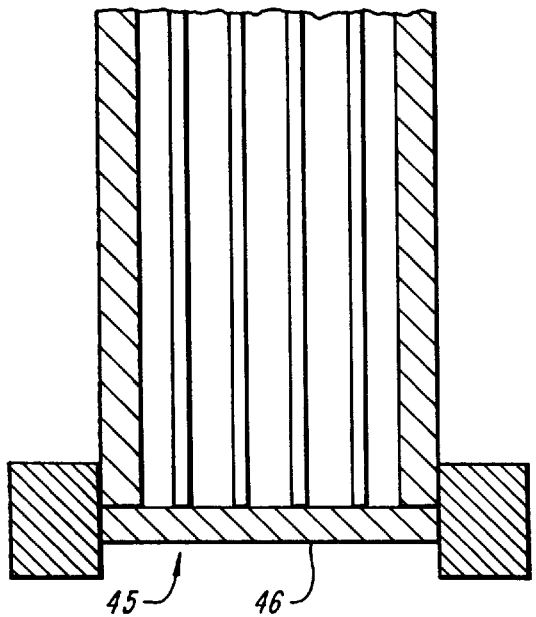

FIGS. 4A–4C illustrate one particularly preferred application of this technique to forming a bundle end 41 on a bundle 40. An annular flange ring 50 is first fitted around a sheaf of rods 5 which are to constitute the bundle. A TIG wire welder 60 with wire 61 then builds up a weld body 40*a* in the ring aperture on the faces of the rods 5 to entirely fill the aperture to a level indicated by phantom fill line 43. A counter bore 45 is then machined into the filled area opposite the bundle to form a precision recess with a thinned acoustically transmissive floor 46.

The bundle assembly 40 terminated in this manner then includes an integral mounting flange formed by the ring 50. Terminated in this manner, the recess 45 may then be pressure-coupled or welded to a second bundle, to make an assembly corresponding to the two-bundle construction shown in FIG. 1. FIG. 4D illustrates such a finished assembly.

Figure 2A:
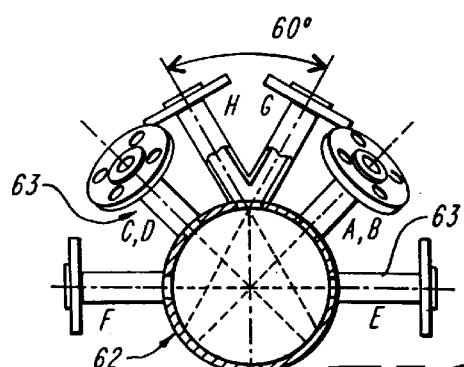
FIGS. 2, 2A and 2B show the link of FIG. 1 in a complex measurement assembly.
Figure 2:
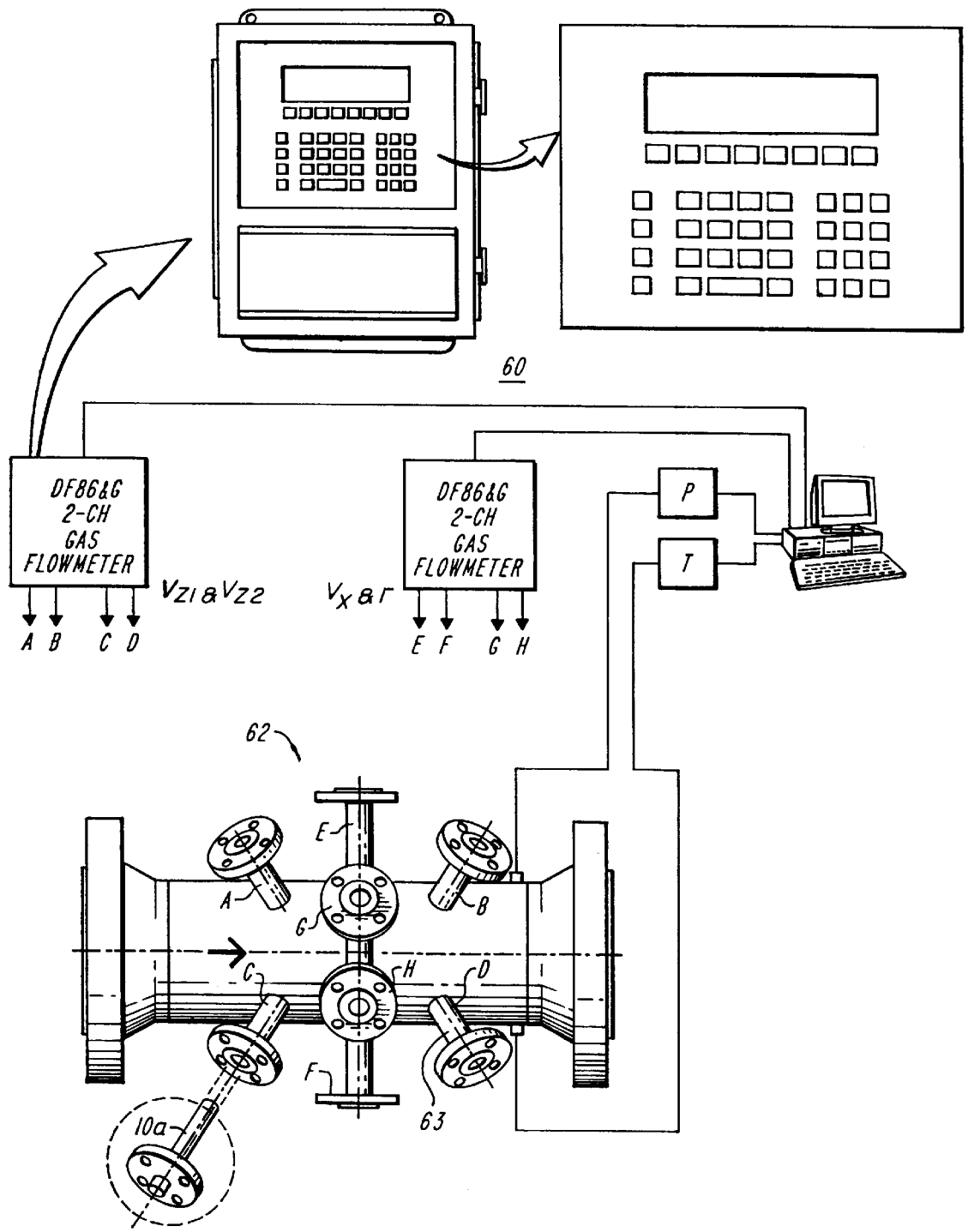

FIG. 2 shows a complex measurement system 60 utilizing bundle buffers as shown in FIG. 1 to non-dispersively carry energy between transducers mounted on to the bundles and precise paths within a conduit.

Figure 2B:
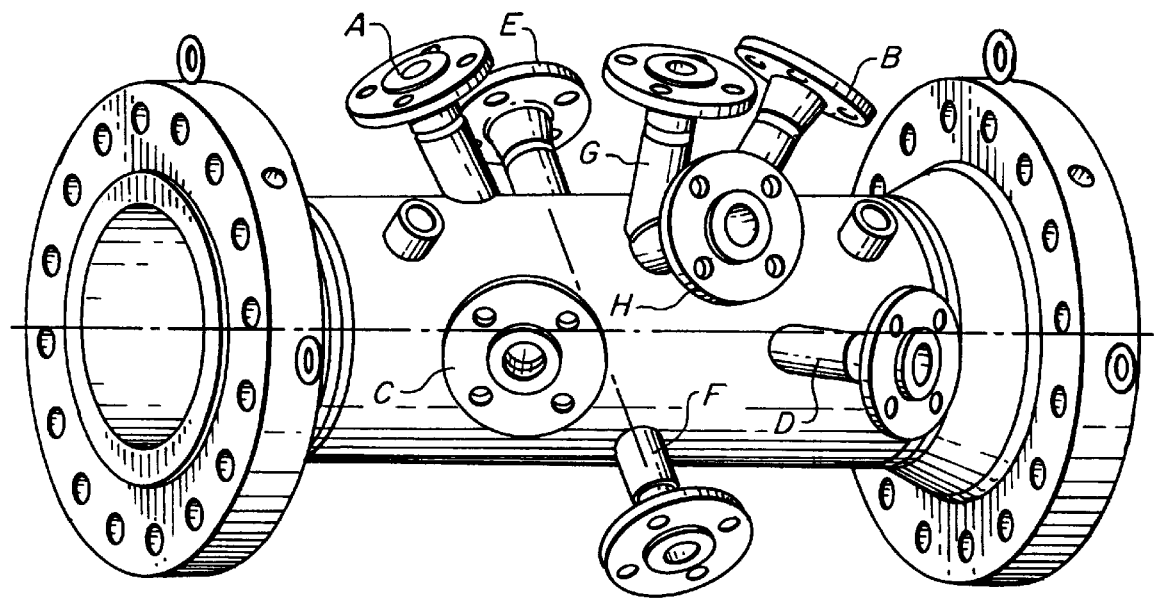

As shown in FIG. 2, system 60 includes a spoolpiece 62 with a plurality of nozzles 63 denoted A, B . . . H oriented for ultrasonic interrogation. Some nozzles (E,F,G,H) are directed along chordal or diametrical paths in a plane to measure cross flow $V_x$ and circulation $\Gamma$ as described in commonly assigned U.S. Pat. No. 5,437,194 issued Aug. 1, 1995, which is hereby incorporated herein by reference. Others are directed along paths having an axial component to sense axial components of flow $V_{x1}$ and $V_{x2}$ in two orthogonal planes. The spoolpiece also contains pockets and sensors for measuring gas pressure P and gas temperature T. FIG. 2A illustrates path configurations of the flange plane nozzles and flow sensing pairs, while FIG. 2B is a perspective view of the spoolpiece. The use of such a spoolpiece for swirl and crossflow corrected measurements is as follows.

In Gauss-Chebyshev or other multipath flowcells, it is well known that the total actual flow $Q_A$ in the axial direction can be well approximated by a linear combination of weighted averages of the flow velocity measured along the several acoustic paths, in combination with an area term. In FIG. 2A, we are dealing with a good approximation to $Q_A$ obtained by the vee paths with the bundles installed in nozzles A, B, C and D. The refinement sought is a small correction or compensation for secondary flows. Let us recognize that the vee paths measure flow in the z direction, that the diametrically opposed nozzles and their bundles measure the crossflow term in the x direction, and lastly, that the $\pm 30°$ nozzles and their bundles, in the plane perpendicular to the pipe axis, measure circulation $\Gamma$. Note also that the units of axial flow and cross flow are m/s but the units for circulation are $m^2/s$. This creates a problem, because we would like to solve for $Q_A$ as a simple linear combination of products of velocities $V_i$ and their respective dimensionless meter factors $K_i$, multiplied by an area term. Let us denoted by $V_{avg}$ the average velocity in the axial direction, the average being taken over the pipe area A. Then $V_{avg}=Q_A/A$.

In matrix notation we want to calculate $V_{avg}=V^T K$. This means we want the sum of the products of $V_x K_x + V_\Gamma K_\Gamma + V_z K_z$ where in the middle term the velocity part is taken to mean the tangential velocity. The tangential velocity is related to the axial velocity by the swirl angle $\psi$, where $\psi = \tan^{-1}$ [(tangential velocity)/(axial velocity)]. By definition, the circulation $\Gamma$ equals the closed-path integral of V dS. Smith et al. (1995) have shown that for the inscribed equilateral triangle path, $\Gamma = 0.605 \, c^2 \Delta t$ where $\Delta t$ is the time difference measured clockwise and counterclockwise and c is the speed of sound in the fluid. Applicants recognize that the tangential velocity is linearly related to V in the formula for circulation. Applicants propose taking as a measure of the tangential velocity, $\Gamma/S$, where for the inscribed equilateral triangle forming the closed path along which $\Gamma$ is measured, $S=3\sqrt{3R}$ where R=internal radius of the pipe.

By deriving a formula for a tangential velocity from the measured circulation, applicants have arrived at a simple systematic way of obtaining the total flow, to be compensated for the secondary flow components, empirically or by experience. In other words, we propose that $Q_A$ be obtained as $AV_{avg}$, where in a manner similar to that used to obtain weights in neural networks, the K's are adjusted until the error in total flow is minimized for the entire range of flow velocities of interest, e.g., $\pm 1$ to $\pm 20$ m/s. As a special case, if the crossflow and swirl are negligibly small, $K_x$ and $K_\Gamma$ would be set to zero. For the vee paths, under turbulent flow, a traditional formula for $K_z$ would be $1/[1.119-0.011 \log Re]$, to be refined as a function of pipe roughness and beam diameter compared to pipe diameter. In general, crossflow and swirl may make some nonzero contribution to the error that needs to be compensated. In that case, their K's are adjusted until that error is acceptably small or until time for further improvement runs out. These points are summarized in the following table where "to be determined" (tbd) means that analytic, experience or trial and error methods are simply iterated until the error is minimized, or until time runs out.

TABLE

| Velocity Term | Mathematical Symbol | Formula in Terms of $c^2 \Delta t$ | Meter Factor $K_i$ |
|---|---|---|---|
| Axial flow | $V_z$ | $\dfrac{c^2 \Delta t}{2L}$ | $\dfrac{1}{1.119 - 0.011 \log Re}$ |
| Cross flow | $V_x$ | $\dfrac{c^2 \Delta t}{2D}$ | tbd |
| Tangential flow | $V_\Gamma$ | $\dfrac{.605 c^2 \Delta t}{3\sqrt{3R}} \Gamma$ | tbd |

In general, it is desirable to employ rods which are so slender, $\alpha \ll \lambda$, that dispersion is very small. We refer to this situation as "dispersionless", "without dispersion" or "non-dispersive" in the practical sense. Theoretically, dispersion is zero only at the origin of the phase velocity vs. $\alpha/\lambda$ curve, or at the high frequency longitudinal wave asymptote. However, by using slightly larger radius $\alpha$, one may operate in a region in which phase velocity in the rods depends on the frequency more strongly, so that higher frequencies travel more slowly. One embodiment of the invention utilizes such rods to form a bundle in a system to launch a signal formed by downchirp Fourier reconstruction (with the highest frequency first, and the lowest last).

Figure 8B:
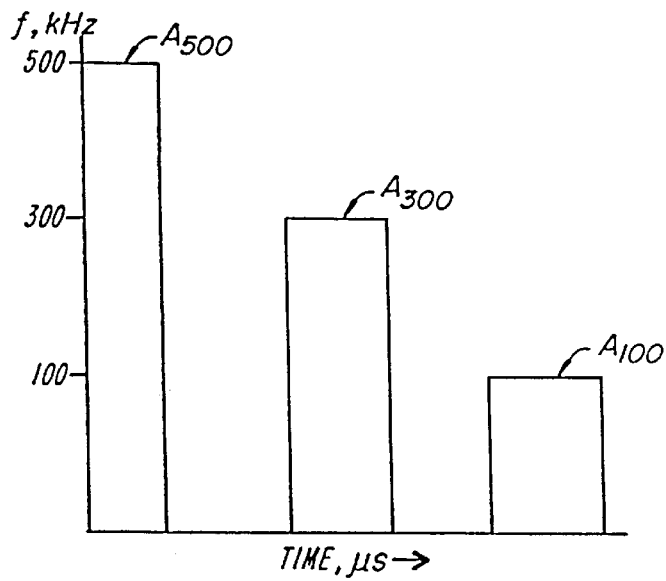
FIGS. 8A and 8B illustrate Fourier synthesis useful with a broadband link.
Figure 8A:
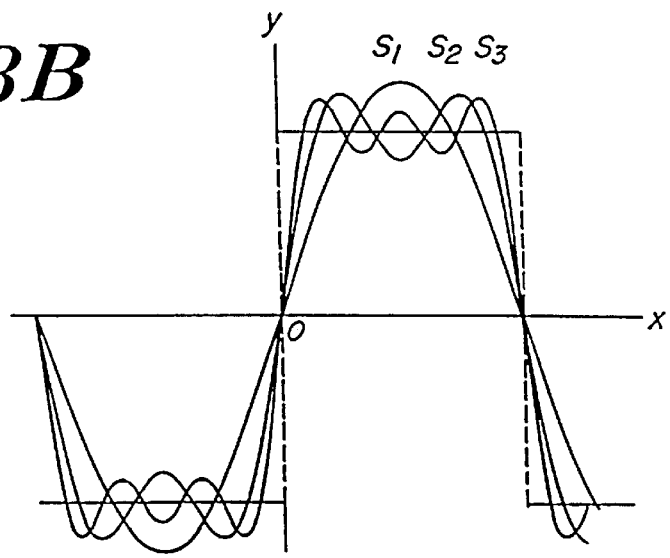

FIGS. 8A, 8B illustrate the signals of such a system. As shown in FIG. 8A, a square wave signal S is shown as a Fourier cosine series summation of a plurality of waves overlapping in a finite time interval. In accordance with the present invention, a nearly square pulse of enhanced edge definition is constructed by actuating the transducer assembly at one end of the buffer to launch, in succession, a series of pulses of different frequencies, e.g., 500 kHz, 300 kHz and 100 kHz at amplitudes $A_f$ (FIG. 8B) corresponding to their coefficients in the desired waveform, at times corresponding to their respective delay times $t_i$ in the buffer. The three separate waveforms then combine at a measurement point to form a well-defined wave by Fourier synthesis.

The precise delay times and amplitudes for such operation may be determined as follows:

Assume for the moment that we are using a symmetric pair of bundles, one on the transmit side, one on the receive side, of a fluid medium. One measures by pulse-echo, measuring the group delay first at 100 kHz, then at 300 kHz and finally at 500 kHz. One also measures the amplitude of each returning packet. Knowing the round trip group delay and amplitude, we can subsequently retransmit amplitude modulated and time delayed tone bursts at the separate Fourier component frequencies, so that they recombine on pulse-echo mode to yield the desired rectangular (or square wave) summation. This yields a precise echo with an edge timing that depends on the temperature of the bundle. As the bundle experiences different temperature profiles, in the course of an application starting up at 20° C., running at 200° C. and occasionally experiencing upsets at 450° C., for example, this pulse echo interrogation provides a dynamical changing time signal which allows the transmitting circuits to be corrected, to maintain the reconstruction at an optimum combination of amplitude modulation and time delay between the different frequency components. Applicant calls this process "dynamic Fourier synthesis," wherein transit time of each component is used to adjust launch time of that component. It will be understood that the above symmetry assumption is convenient for the sake of explanation but is not necessary. One can interrogate each bundle separately and use the average of the round trip delays and amplitudes, to calculate the necessary delay and modulation for each component. A further refinement is to consider that the different frequencies will be attenuated differently by the fluid medium, especially if it is turbulent. To compensate, the higher frequencies are transmitted more strongly than if there were no attenuation in the fluid or attenuation were the same for all Fourier frequencies A simple processing algorithm or neural network may be set up to determine reasonable transmitting adjustments, so that the received packet is as nearly rectangular as possible. In fact, deviations for the ideal rectangular result may be interpreted in terms of fluid characteristics, e.g., turbulence. The default transmission would be the combination of time delays and amplitude modulations that makes the averaged pulse echo return as rectangular as practical. In other words, the default transmissions disregards any corrupting influence the fluid medium may have on the packets.

In operation, the three tone bursts are transmitted into a first bundle in rapid succession, say 500 kHz first, followed by 300 kHz, followed by 100 kHz, delays between tone bursts being controlled by amounts as indicated above. The lower-frequency tones gradually tend to catch up with the 500 kHz tone burst, their delays being selected such that due to total length of the transmitting and receiving bundles catching up occurs essentially at the receiving transducer. In this way, the three tone bursts add up to reconstruct a rectangular pulse whose leading edge is sharper than that of any of the tone bursts alone. In this way a time-of-flight ultrasonic system is made more accurate and less subject to skipping a cycle. The Fourier-reconstructed rectangular pulse is a very distinct waveform, easily recognized, not easily confused, and its arrival time can hence be determined reliably and precisely.

Another system embodiment utilizing the broadband bundle buffer but not involving Fourier reconstruction is to transmit a pair of closely-spaced frequencies such that they both would experience nearly identical time delays in the buffers, and then to measure these delays by pulse-echo techniques. The unknown time in the medium between the buffers is then determined by subtracting the buffer times from the total time of travel. Here the skipped cycle problem is solved by finding the transit time in the medium that give the best agreement for both frequencies. The skipped cycle then shows up at the beat frequency, that is, at half the difference frequency. The error now due to skipped cycle becomes in effect so large as to be clearly recognized and hence disregarded or easily compensated.

Returning now to the buffer bundle, applicant envisages a number of specific variations employing a directed and guided non-dispersed link element as detailed above. FIGS. 9A–9E illustrates details of system implementations.

Figure 9A:
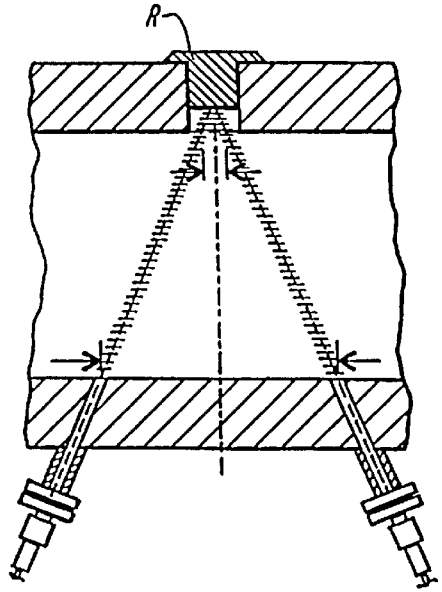
Figure 9C:
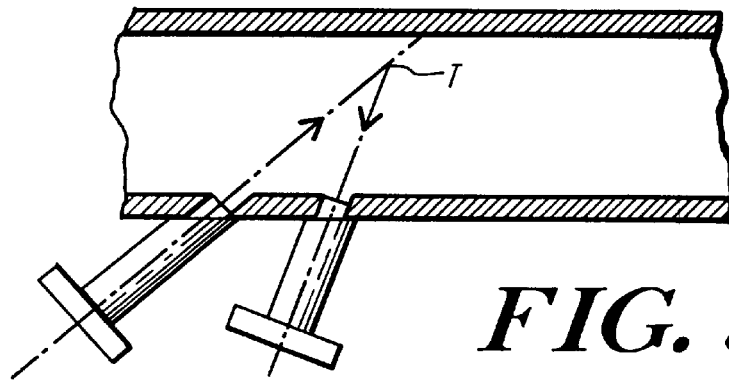

As shown in FIG. 9A, the axial symmetry and elongated body of the bundle buffer allows them to be aimed with high precision for V-path interrogations. A simple reflector R may be configured as a plug element between two directed nozzles to define a flow measurement path. For chordal interrogations, a 180° reflector R' may be used as shown in FIG. 9B. More generally, the nozzles may be oriented at different angles so that the transmitted and received signal paths intersect in a target region T within the fluid, as shown in FIG. 9C. This allows detection of scattered signals from localized regions, and may be used with various known measurement protocols.

Advantageously, the bundle buffers of the present invention not only allow a well-defined signal to be delivered to or from a point at or in the measured fluid, but also allow the orientation or shape of beam to be precisely controlled. These properties enable transducers to be arranged in systems such as the following:

a) a multipath flow meter with off-diameter chordal vee paths wherein all transducers are on one side of the conduit;

b) a flow meter wherein the transducers for upstream (U) or downstream (D) interrogation are mounted in common flange planes, which may coincide;

c) a measurement system wherein radiated beam pattern and direction in the fluid are controlled by varying frequency applied to a bundle of non-uniformly distributed rods.

The bundle may be sized to press-fit into the nozzle, and may have its face F finished to lie flush with the pipe interior wall so as to present no flow disturbances. FIGS. 9D and 9E illustrate orthogonal sectional views of such a cylindrically faced bundle. As further shown in FIG. 9F, the outer shell near the face may be stepped so that only the very end is a press fit. This assures better acoustic isolation from the pipe and nozzle, while assuring that the assembly will be removable if required.

Figure 10A:
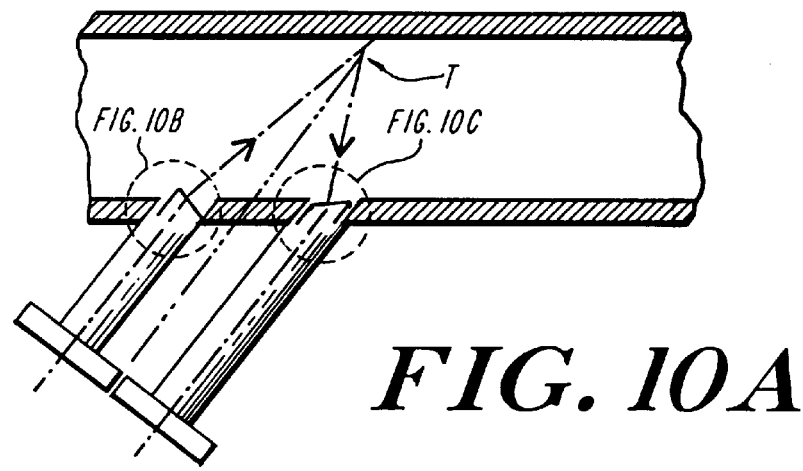
FIGS. 10A–10C show details of a parallel bundle system with crossed beams.
Figure 10B:
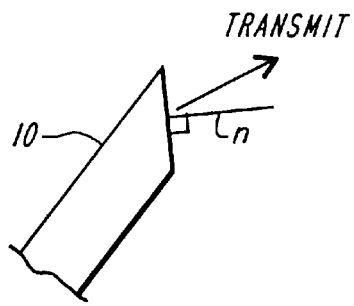
Figure 10C:
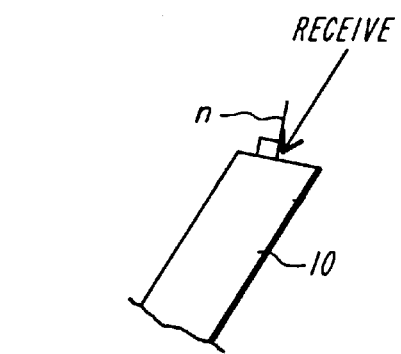

As illustrated in FIGS. 10A–10C, when used in a nozzle in this manner, a further degree of path control is achieved by the termination or end-face of the bundle. FIG. 10A shows two parallel nozzles for holding bundles with end faces shaped to intersect in the fluid stream. The transmitting bundle has its face chamfered to face toward the receiver as shown in FIG. 10A, while the receiver bundle has it face chamfered facing in the other direction such that each beam follows the desired refraction angle to intercept the other beam in the fluid. The beam spread may further be controlled by lens-like deviations in the face contour, or the refraction angle may be varied to compensate for flow-induced changes by changing the frequency of the signal to raise or lower its soundspeed in the bundle. As with the bundle of FIG. 5, a lens, wedge or reflector may be incorporated into the non-dispersive link.

The invention contemplates another type of beam control achieved solely by the constituent rods forming the bundle. In accordance with this aspect of the invention, the rods forming the non-dispersive waveguides within the bundle are not all identical, but instead are formed of several different groups of different sizes arranged to form a focused, dispersed or deflected output or reception beam. FIGS. 11A–11F show the construction of such embodiments.

Figure 11:
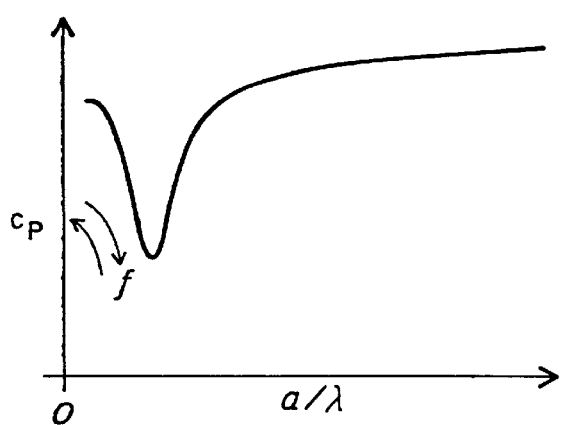
FIGS. 11–11C illustrate more complex bundle constructions.

FIG. 11 shows the dependence of soundspeed in a thin rod on the ratio of radius $\alpha$ to wavelength, based on the work of Tu et al. (1955). For the embodiments described below, the rod radii are selected to lie in the initial sloped (small α) shoulder of this distribution.

Figure 11A:
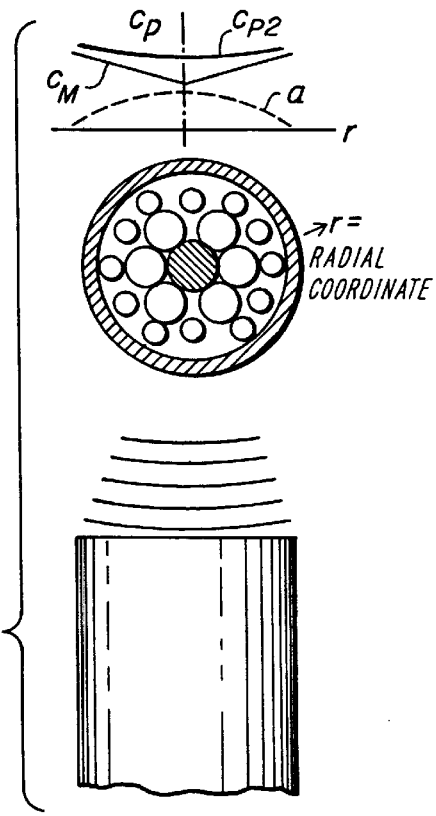

As shown in FIG. 11A, one embodiment of a bundle 100 illustrated in cross section has rods which are of smaller diameter at its periphery than at its center, where the range of diameters (e.g., 0.25 to 1.5 mm) is selected so that the soundspeed in the rods varies with rod diameter, i.e., with radial position in the bundle. Soundspeed Cp increases with radial position, and the bundle therefore acts like a convex lens, producing a convergent output beam. Similarly, as shown in FIG. 11B, a bundle with larger rods at its periphery forms a divergent beam. The bundle need not be a round cylinder. FIG. 11C shows a bundle formed as a rectangular or round stack of rods of graded radius that increase in the x-direction rather than radially. This is analogous to a linearly graded index of refraction, and the Poynting vector forms a fixed dihedral with respect to a plane normal to the launching face. In that construction, the output beam in launched at an angle to the normal plane.

Neither is it necessary that the individual rods or wires making up the bundle be round. Hexagonal or square wire or rods may be used. However, round is the preferred shape to minimize edge contact, and avoid the possibility of coupling, mode conversion, leakage, and other dispersive or attenuating processes.

Figure 12:
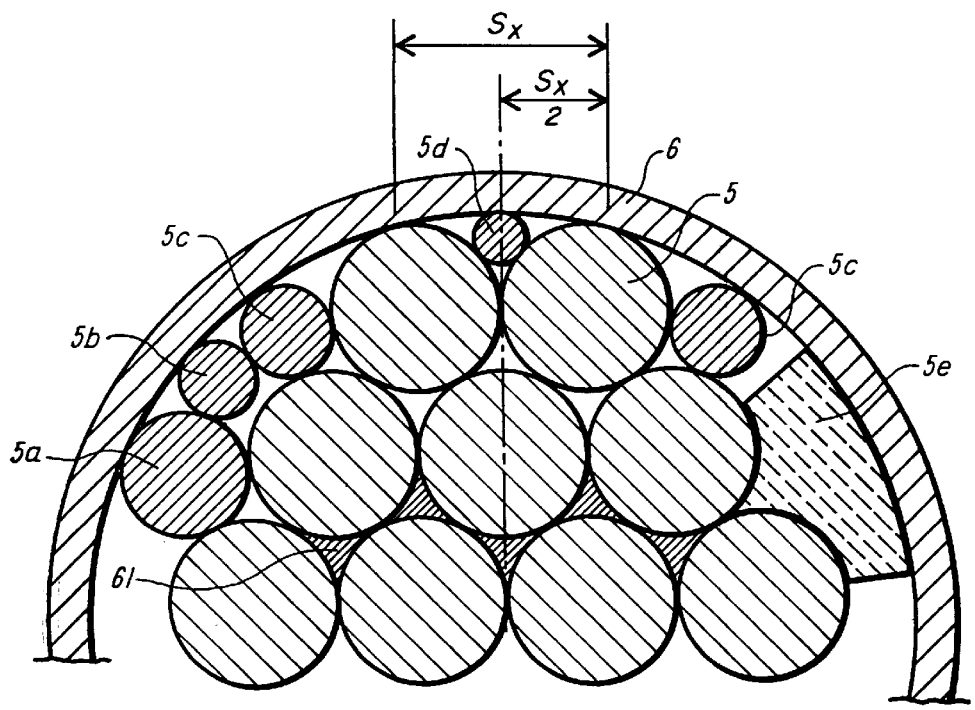
FIG. 12 illustrates techniques of bundle reinforcement.

FIG. 12 shows another construction in which not all of the waveguide elements are of one diameter, e.g., like the one denoted 5. Here, to reduce the span of the thin containment shell by half, from $S_x$ to $Sx/2$, a filler rod 5d of somewhat smaller diameter is introduced to fill one of the cusps. In the arrangement illustrated, not all cusps are of equal size and hence different filler waveguides are used denoted by 5a, 5b, 5c, and 5d. These are all round wires (round rods). A special shaped filler waveguide 5e is also shown having a somewhat trapezoidal cross section. The largest cross sectional dimension of any of these should be small compared to wave length so that the compressional wave phase velocity will be essentially equal to the square root of Young's modulus E divided by the density p. One could also fabricate a metallurgically-secured bundle, held together by welding or brazing at least at both ends and optionally reinforced at one or more localized points along the length of the bundle, and then machine the exterior rods until a round-bounded pattern is achieved. Machining could be done by electrical discharge machining, electrochemical machining, or grinding, or by other known means, such as temporarily bonding the rods together, turning to a desired outer diameter, then removing the temporary bonding agent. The machined bundle could then be installed in a sleeve whose inner diameter matches the bundle outer diameter.

Also shown in FIG. 12 is a filling material 61 at some of the central cusps. This material is introduced to attenuate pulses and is preferably distributed along the axial direction over a substantial length, but not near the ends where heat introduced during welding or brazing would disbond the waveguides from the intended damping material, which may, for example, be epoxy, urethane, silicone rubber or a ceramic or graphite paste.

More broadly, the non-dispersive rods which form a bundle need not be a densely packed bundle of "solid" rods, but may be any well-packed array of suitable non-dispersive members, where well-packed is understood to mean that they are sufficient in number or total cross-section to effectively carry enough signal energy, and they are packed with little enough contact so that they do not couple or become dispersive as a group.

Figure 13:
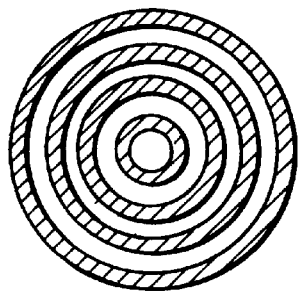
FIGS. 13, 13A–13D illustrate hybrid and other embodiments of the invention.
Figure 13A:
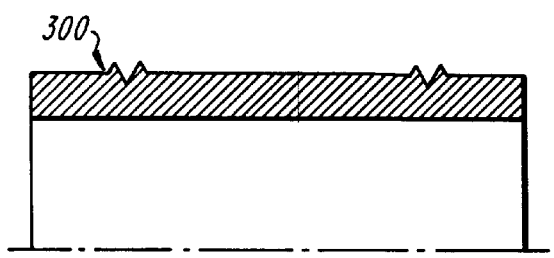
Figure 13B:
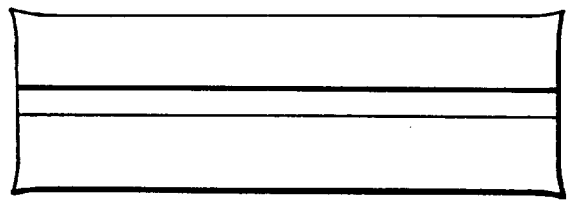
Figure 13C:
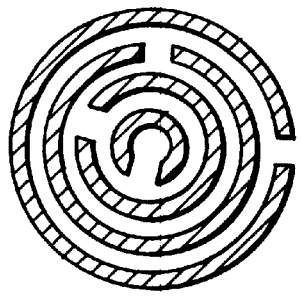
Figure 13D:
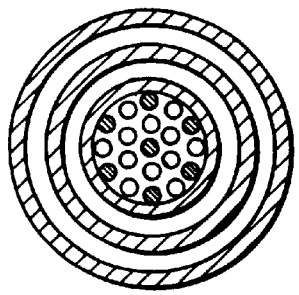

This may be accomplished using a set of hollow tubes arranged concentrically as shown in FIG. 13. The tubes have been formed with slight isolated protrusions to keep them separated and essentially out of contact with each other. Such protrusions may for example consist of slight dimples 300 raised with a prick punch as shown in FIG. 13A to contact the adjacent exterior tube, slight circumferential indentations made with a dull tubing cutter, or flared ends as shown in FIG. 13B to contact the nested exterior tube. The tubes may also be arranged in a bundle as shown for the non-dispersive rod embodiment described above, within a common sleeve. Other methods of isolation, such as isolated spot welds, affixing a spiral spacer wire between adjacent surfaces may also be used. Similarly, rather than a concentric arrangement of mutually isolated hollow tubes, a series of concentric split pins (thin cylinders with an axial slot) may be used, as shown in end view in FIG. 13C. The invention also contemplates hybrid bundles with a plurality of non-dispersive rods enclosed within one or more hollow cylinders, as shown in FIG. 13D.

The bundle buffer of the present invention also may be implemented in other versatile constructions to solve problems of pipe fitting complexity or flow path accessibility.

For example the 90° reflector embodiment shown in FIG. 5 may be readily incorporated in an oblique mounting construction which accesses a process flow line to take flow sensing measurements without dead space. Such a system 500 is shown in FIG. 5A. Here, a bundle 1 having a reflector 1 a is fitted obliquely through a simple flange 3 to cap a fluoropolymer-lined tee in a process line and to inject or receive a signal obliquely along a flow sensing path P. The bundle sheath may be welded where it passes through the flange with a circumferential weld 4 to seal and support the bundle shell. Advantageously, in processes requiring high corrosion resistance, this property is provided by simply utilizing a titanium or monel flange, and it is not necessary to fabricate a high quality and specially machined spool-piece or angled nozzle conversion assembly.

FIG. 5B shows one construction for the launching/receiving termination of the bundles of FIG. 5A. In this construction, the bundle buffer 9 has an angle wedge 19 in the form of a cap. The signal path from the rods in the bundle 9 reflects off the oblique face W internally of the wedge and is directed to launching face 29 at right angles to the bundle end. A quarter wave matcher 11a, shown in phantom, may be provided on the launching face. The reflection is internal, assuring stable non-fouling alignment, and the wedge may be simply coupled to the end of the bundle, for example by providing straight (non-tapered) threads on the cap interior, or by providing a plurality of outwardly pointing set screws 28 to secure the wedge on the bundle while drawing it down into pressure contact with the bundle face. The wedge may be made of a low thermal expansion material, such as molybdenum or Kovar, allowing a simpler expansion matching when welding or otherwise attaching a graphite λ/4 matching plate.

Figure 14:
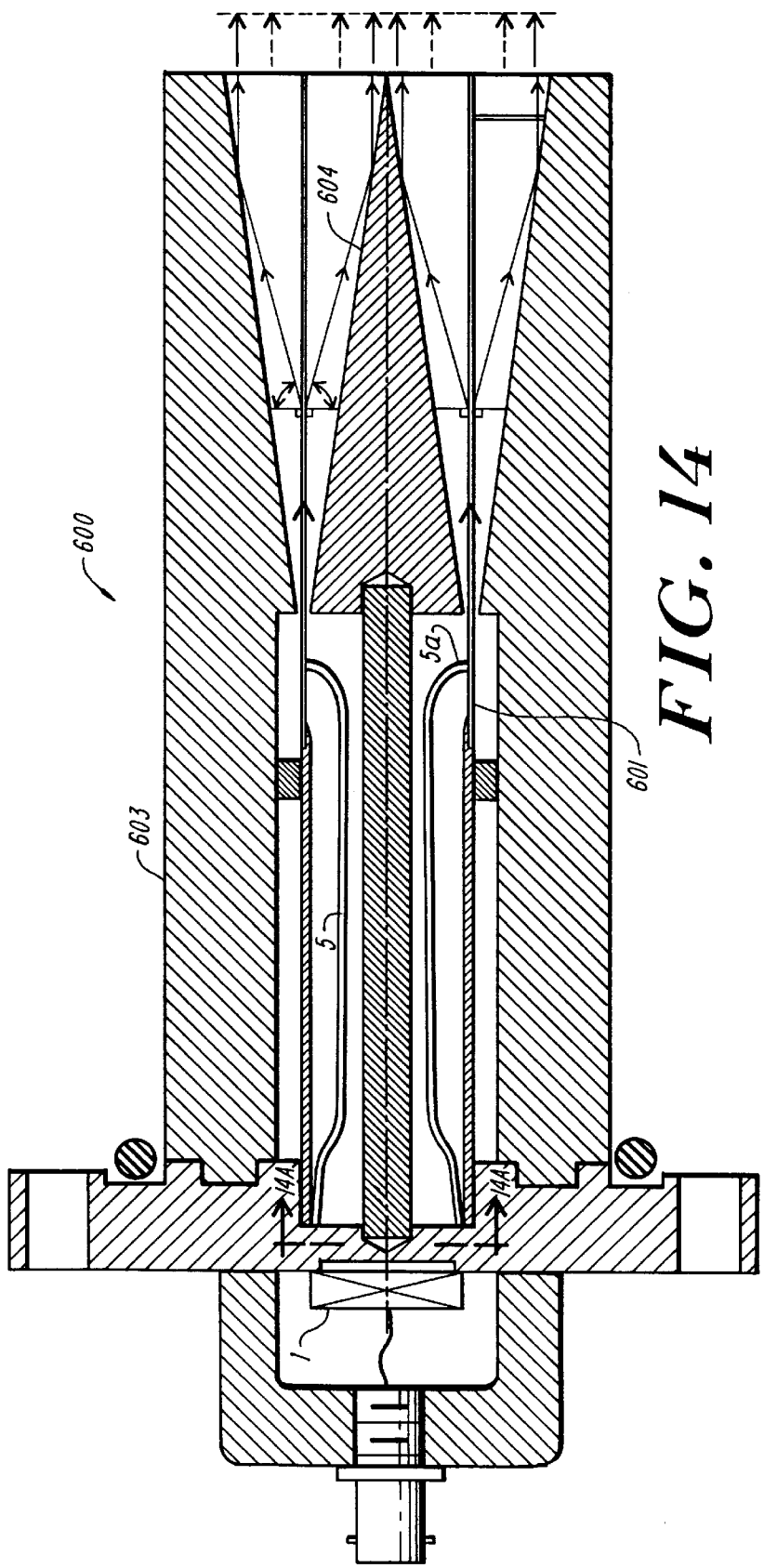
FIG. 14 illustrates a mode-converting link of the invention in an impedance-matching embodiment.
Figure 14A:
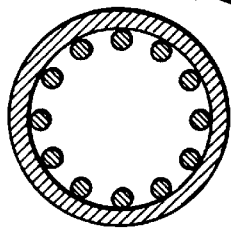

While the foregoing description has focused on the fabrication of a non-dispersive acoustic path link that may be a bolt-in replacement for or improvement of much existing process "plumbing", and particularly to straight or rigid wave guides, the invention also contemplates constructions in which the assembly is not necessarily straight, and in which the rod termination may involve mode conversion or other features. FIG. 14 illustrates an embodiment 600 wherein a crystal 1 contacts a peripheral band of a centrally-thinned flange to direct its energy into a plurality of rods 5 which extend from the flange mount position to a distal end 5a. The distal ends flare out to contact a thin cylindrical shell 601 at normal incidence and mode-convert their signal to a flexural wave that propagates along the cylinder. An outer sleeve 603 with an outwardly tapered mouth and an inner cone 604 with an inwardly tapered point are spaced outside of, and inside the cylinder, respectively. These conical reflectors reflect the compressional waves formed in the surrounding gas by the surface waves launched in cylinder 601, forming a plane wavefront.

Advantageously, the non-dispersive bundle of this invention remains quiet between pulses and end echoes, allowing many different measurements to be performed during discrete time intervals.

Figure 10D:
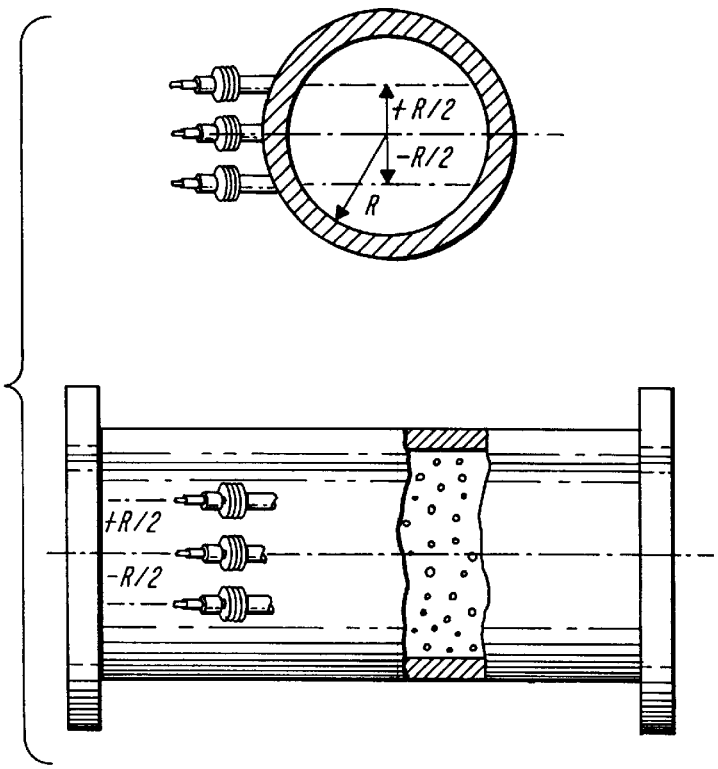
FIGS. 10D and 10E illustrate elements of the invention in pulse-echo and in pitch-catch sensing arrangements, respectively.
Figure 10E:
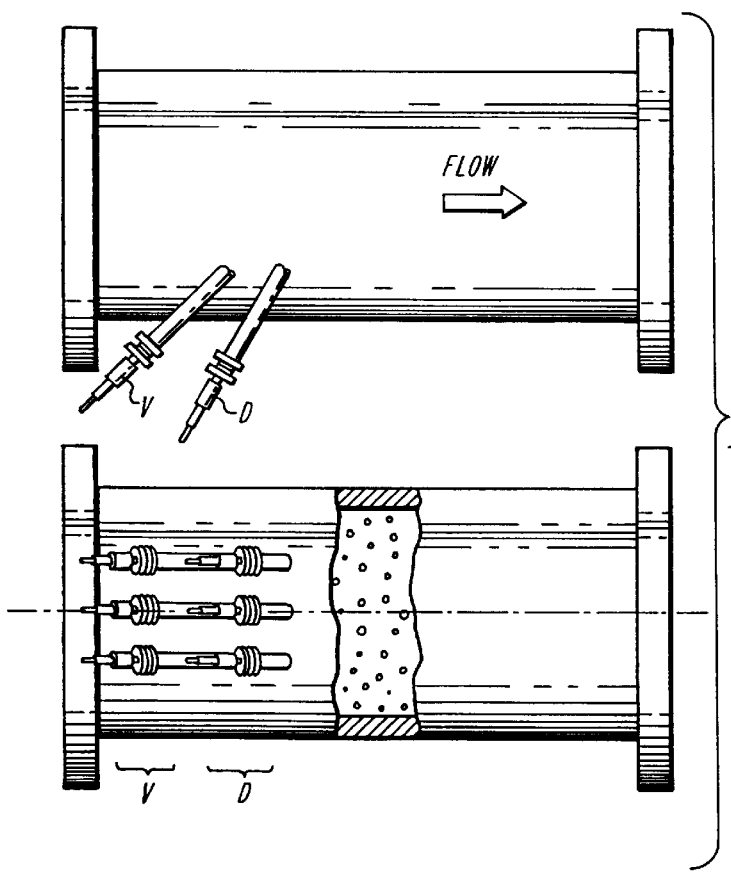

The piece-wise or window-wise quiet bundle may be used in pulse-echo interrogation of fluids, e.g., range-gated Doppler as noted by Brandestini (1978), the key system elements being those described in a 1979 chapter on Ultrasonic Flowmeters, p. 438, FIG. 19(a), authored by one of the applicants. In FIGS. 10D and E, we show two configurations (D, pulse-echo, and E, pitch-catch) to obtain range-gated flow information from the horizontal diameter plane and from upper and lower midradii planes. These measurements utilize the energy scattered off turbulent eddies or off particulates or bubbles in the fluid. Note that sets of flanges could be bolt-hole-aligned for (a) ease of fabrication and for (b) ease of interpreting scattered-energy test data. In the pitch-catch case, nozzles may be parallel if the bundles are suitably beveled, as described above. Note that, because the bundle allows the radiated beam to be launched into the fluid at angles other than perpendicular to the end, it is possible to align upstream U and, separately, downstream D flanges, and even U and D flanges all in one plane so that the U and D planes coincide.

Because of this quiet aspect, due to lack of reflections along the length of the rods, it is possible to monitor the efficiency of coupling of one rod bundle to another, and also to monitor the end echo where the sound wave enters the gas or fluid stream. This can be done at each frequency of interest, e.g., 100, ..., 500 kHz, as shown in the signal trace of FIG. 4D.

Figure 1B:
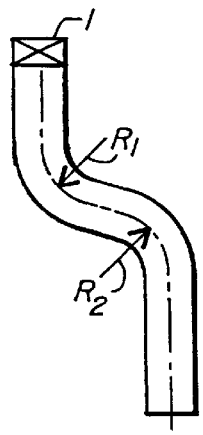
FIGS. 1B and 1C show particular bundle embodiments.
Figure 1C:
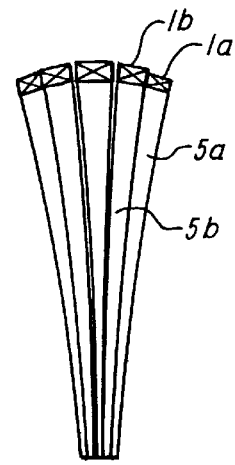

We note further that certain special features, such as forming an S- bend to prevent nuclear streaming out of an otherwise straight access port (i.e., utilize an S-port); tapered rods to concentrate the sound, as shown in FIG. 1C, or radiate, or to diverge the sound, to allow the directivity benefits of a flared, large-aperture radiating end to be realized; the use of electronically time delayed impulses, to synthesize a particular waveform depending on how different energizing components (not necessarily Fourier components) are introduced and subsequently delayed as a function of their radius/wavelength ratio. Applicants further recognize the possible alternative construction where the bundle is rigid but curved, as shown in FIG. 1B to maintain identical rod lengths (the S-bend being one example). A different construction is to employ a braided flexible cable for the bundle allowing greater flexibility of installation or tank movement.

Figure 15:
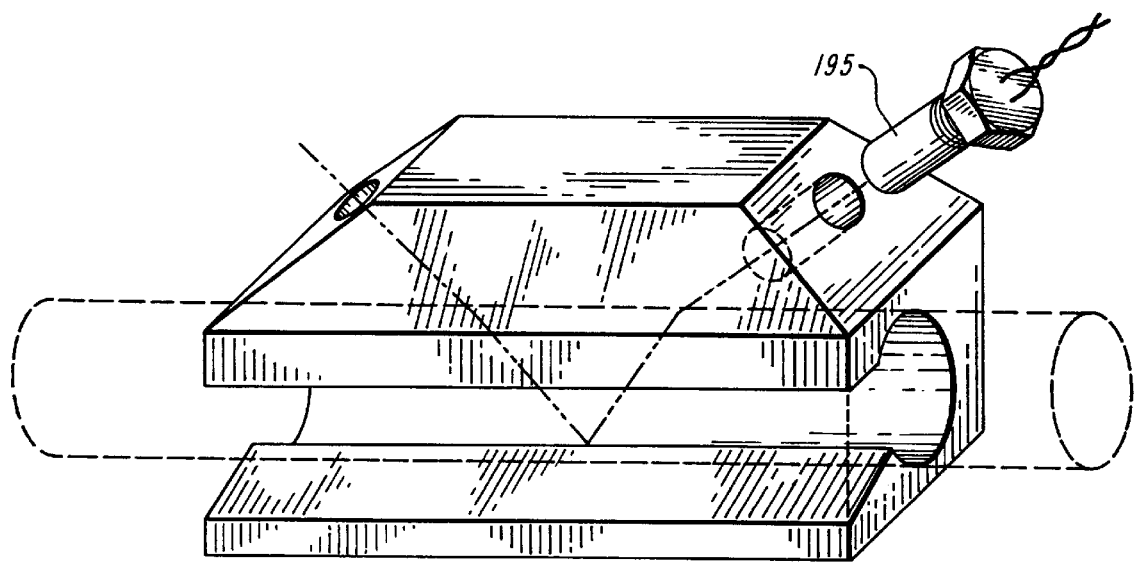
FIGS. 15 and 15A illustrate a clamp-on embodiment.
Figure 15A:
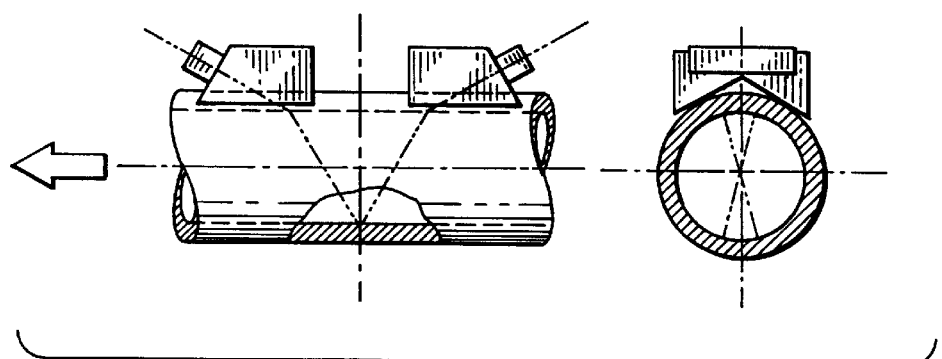

The non-dispersive links of the present invention may also be employed in clamp-on transducer systems, wherein a mounting block 70, as shown in FIGS. 15, 15A is fastened to a conduit in a position such that transducer 75 held therein launches an ultrasonic signal along a precisely defined path through the pipe wall and fluid flowing therein. A number of such clamp-on blocks and special interrogation paths are shown in commonly-owned U.S. Pat. No. 5,179,862 which issued Jan. 19, 1993, which patent is hereby incorporated herein by reference. FIG. 9A of that patent illustrates a block assembly wherein the transducer has an elongated nosepiece denoted 195 therein, which extends through the wedge or mounting block and is urged into contact with the pipe wall. In accordance with a further aspect of the present invention, such a transducer nosepiece is formed of a non-dispersive guide bundle as described above, to convey the signal between the actuation crystal or other transducing element, and a contact face which contacts the pipe at an appropriate incidence. For example, the coupling face may have a curvature matching the pipe to continuously and non-dispersively couple into the pipe wall, may have a splitter configuration or point- or knife-edge to launch shear or other waves for a pipe wall measurement, or other known contact coupling face.

Figure 16A:
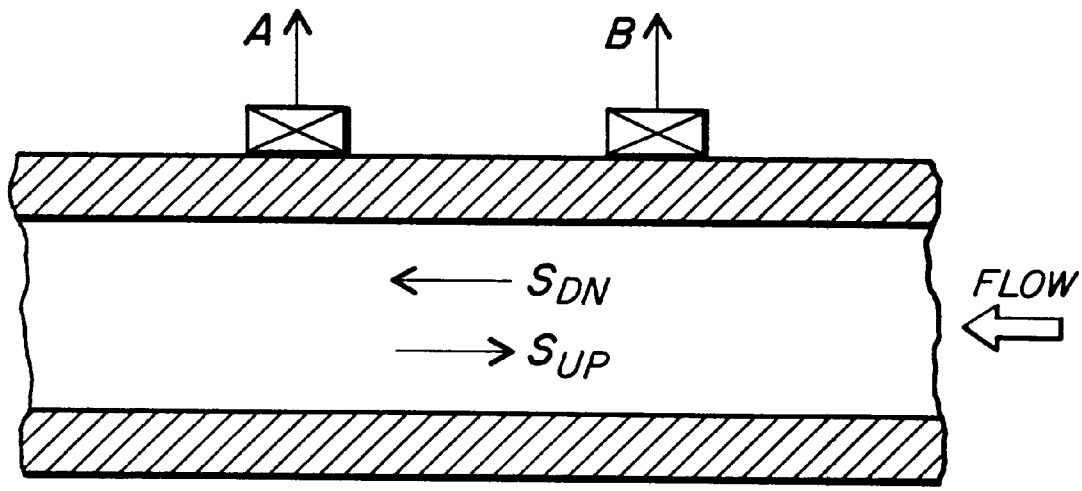
FIGS. 16A and 16B illustrate measurement systems of the prior art and the present invention, respectively.
Figure 16B:
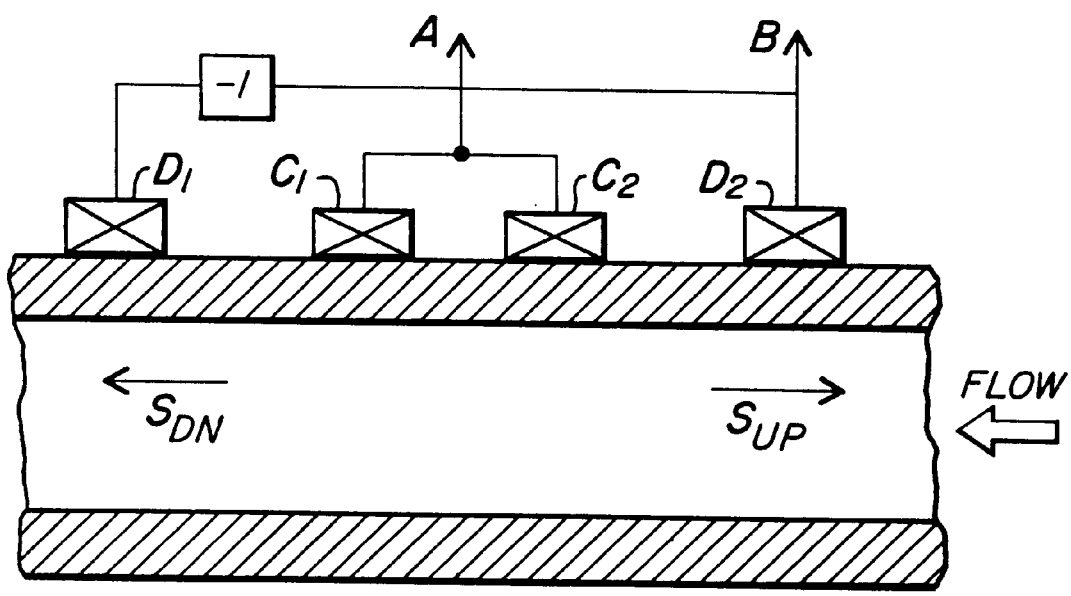

According to another aspect of the invention, transducers coupled to a wall are interconnected to provide noise cancellation. FIGS. 16A and 16B illustrate operation of this embodiment. FIG. 16A shows a prior art system wherein two transducers, denoted transducer A and transducer B are mounted on a conduit to transmit and receive counter propagating upstream and downstream signals. The downstream-propagating signal received at transducer A is denoted $S_{DN}$, while the upstream signal received a transducer B is denoted $S_{UP}$. In general, the received signal will contain a useful component which has propagated through the liquid, denoted $S_{LDN}$ and $S_{LUP}$, respectively, and will contain a noise signal denoted $N_{DN}$ or $N_{UP}$, respectively. A major part of this noise signal is acoustic short circuit noise which has propagated through the steel wall and therefore arrives at both transducers after the same time delay, whether propagating in the pipe wall in the upstream or downstream direction.

FIG. 16B shows a system in accordance with this aspect of the invention. A first transducer assembly C shown as consisting of two elements $C_1$ and $C_2$ transmits signals in an upstream and a downstream direction. A pair of receiving transducers D, consisting of receivers $D_1$ and $D_2$, receive the upstream and downstream waveforms and their outputs are combined 180° out of phase. The transmitting assembly C, while shown as two elements, may consist of a single transducer provided that transducer is set up to launch waves that propagate in both directions. For example, transducer C may have a splitter and contact the pipe to launch shear waves bidirectionally. The combined output signal from the transducers $D_1$ and $D_2$ will effectively cancel almost all conduit noise originating locally. The resulting signals are processed by a differential correlation process in order to determine a precise time delay incurred in signal travel. A detailed description of correlation processing and suitable coding or signal wave trains are described in commonly-owned U.S. Pat. No. 4,787,252 entitled Differential Correlation Analysis, issued on Nov. 29, 1988. That patent is hereby incorporated herein by reference in its entirety.

Briefly, by correlating the combined received signal with a delayed replica of the transmission signal, a very precise $\Delta t = T_o$ is obtained. Using h(t) to represent $S_{UP} - S_{ND}$, if there is no flow, h(t) is almost zero. If there is a flow, then h(t) is the function of $T_o$, where $T_o$ is the time delay between $S_{UP}$ and $S_{DN}$.

To find $T_0$ from h(t), one can use a known function g(t) selected is such a way that it has similar shape to signal $S_{LDN}$ (or $S_{LUP}$). This may be a replica of the transducer actuation signal.

The cross correlation function $f(\tau,T) = \int h(t)[g(t-\tau-T)-g(t-\tau)]dt$ will reach its maximum when $T=T_0$.

Figure 17:
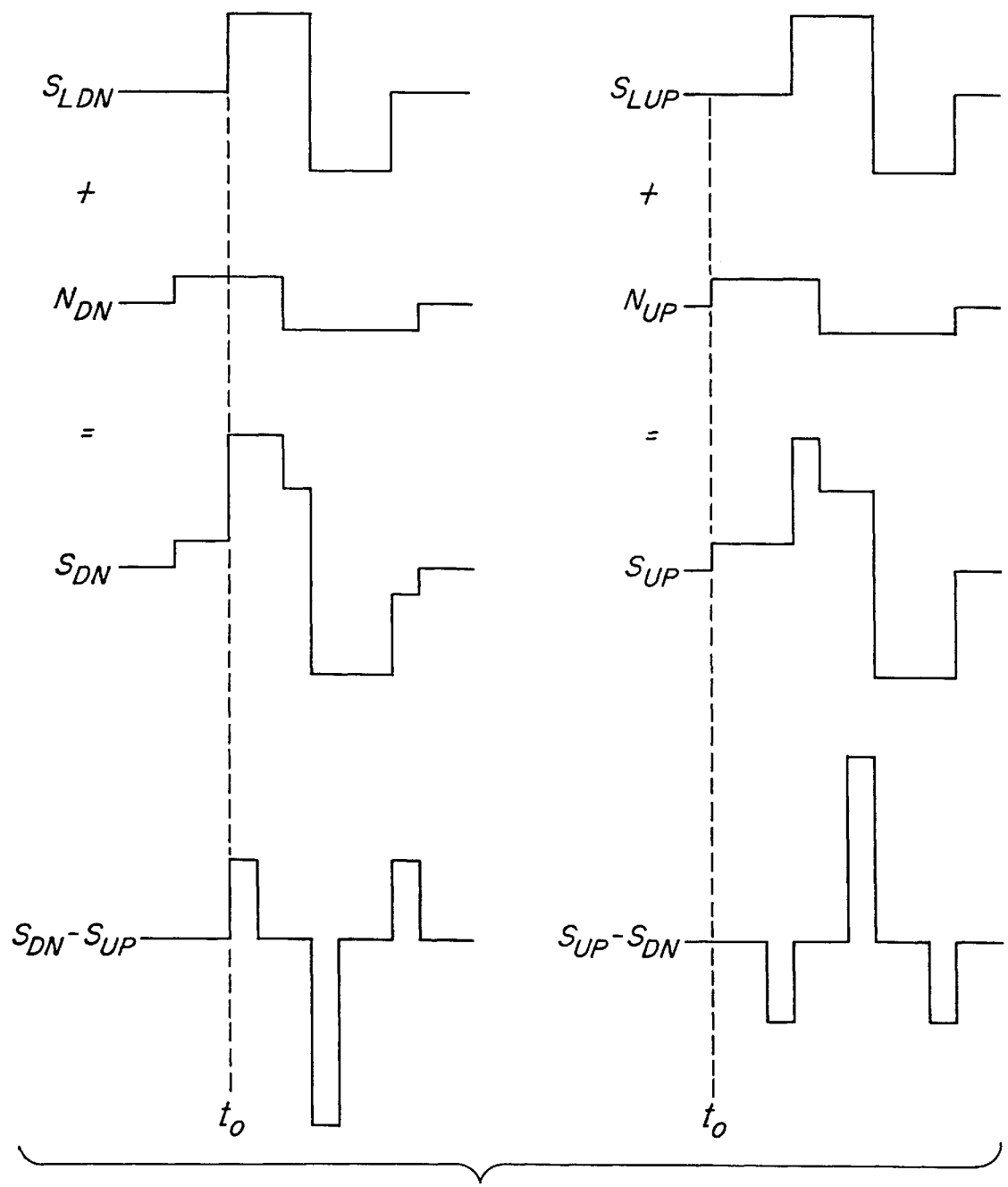
FIG. 17 illustrates operation of the system of FIG. 16B

FIG. 17 illustrates the signal traces involved, showing noise cancellation achieved by combining the two signals out of phase and processing the combined signal in this manner.

This approach to noise cancellation for eliminating common-mode noise may also be implemented using only two transducers, as in the configuration of FIG. 16A. The upstream and downstream signals may be transmitted simultaneously, or upstream and downstream interrogation may be performed alternately (but at times sufficiently close to assure that common flow conditions prevail) to implement a "delayed common mode" noise cancellation. In this case, the processor preferably stores the received waveforms propagating in each direction, then combines them and performs correlation analysis.

The invention being thus described, variations, modifications and adaptations thereof will occur to those skilled in the art, and such variations, modifications and adaptations are considered to be within the spirit and scope of the present invention, as defined in the claims appended hereto.

We claim:

1. An ultrasonic measuring system characterized by an enhanced signal path comprising a signal conductor interposed as a link in the signal path to conduct an ultrasonic measurement signal pulse at least partway between a transducer and a process fluid environment, wherein the signal conductor includes a plurality of rods each having a first end, a second end and a defined diameter and length, said diameter being sufficiently small to propagate an effective measurement portion of the signal pulse between its first end and its second end, and a terminating sheet of material continuous with said first ends and configured to acoustically couple said effective measurement signal portion into and out of said rods wherein the rods are bundled together in tight mutual contact within a sealing enclosure together with said terminating sheet of material to form a rigid sealed assembly for mounting in the transducer signal path such that the assembly conducts and couples a directed beam of said effective measurement signal portion between said process fluid environment and said transducer while providing both thermal separation of and effective sealing between the transducer and the fluid environment.

2. An ultrasonic measuring system according to claim 1, wherein said signal conductor includes a quarter wave plate mounted for matching to a surrounding medium.

3. An ultrasonic measuring system according to claim 1, wherein the signal conductor further includes at least one transducer coupled into one end of said rods.

4. An ultrasonic measuring system according to claim 3, wherein the transducer is operable at a plurality of frequencies substantially given by {nf} where n=1, 3 . . . is an odd integer and further comprising an antireflection plate dimensioned for transmitting waves of at least two of said plurality of frequencies.

5. An ultrasonic measuring system according to claim 4, further comprising means for automatically evaluating signal quality at each of said plurality of frequencies and, responsive to said evaluation, for operating a highest frequency of said plurality that propagates with useful signal quality.

6. An ultrasonic measuring system according to claim 1, wherein the terminating sheet is formed of counterbored fill weld material.

7. An ultrasonic measuring system according to claim 1, wherein said plurality of rods are enclosed and packed within a shell having a wall thickness such that speed of symmetric Lamb waves in the shell substantially matches speed of the signal in the rods.

8. An ultrasonic measuring system according to claim 7, further comprising spacer elements extending parallel to and located between said rods for structurally supporting said shell.

9. An ultrasonic measuring system according to claim 7, wherein said shell has thickness greater than diameter of the rods.

10. An ultrasonic measuring system according to claim 1, wherein said plurality of rods have different radii and are arranged in an ordered pattern to differentially delay transmission of acoustic energy so that different portions of the sheet receive propagated energy at different times causing the sheet to launch a shaped or deflected output beam.

11. An ultrasonic measuring system according to claim 1, wherein said signal conductor extends from a pressure boundary to a fluid at high pressure for carrying a transducer signal coupled thereto, and further comprising a transducer, said transducer being coupled through said pressure boundary by a rigid bundle of rods by a coupling that decouples to remove the transducer without breaking the pressure boundary.

12. An ultrasonic measuring system according to claim 1, wherein said system operates in a pulse-echo mode and the signal conductor both sends a signal and receives back said signal for performing a measurement.

13. The ultrasonic measuring system of claim 1, further comprising timing means configured to form an effective measurement signal of enhanced edge definition from plural frequencies conducted at different phase velocities in said plurality of rods.

14. An ultrasonic buffer comprising a signal conductor for interposition as a link in the signal path to conduct an ultrasonic measurement signal pulse at least partway between a transducer and a process fluid environment, wherein the signal conductor includes a plurality of rods each having a first end, a second end and a defined diameter and length, said diameter being sufficiently small to propagate an effective measurement portion of the signal pulse between its first end and its second end, and a terminating sheet of material continuous with said first ends and configured to acoustically couple said effective measurement signal portion into and out of said rods wherein the rods are bundled together in tight mutual contact within a sealing enclosure together with said terminating sheet of material to form a rigid sealed assembly for mounting in the transducer signal path such that the assembly conducts and couples a directed beam of said effective measurement signal portion between said process fluid environment and said transducer while providing both thermal separation and effective sealing between the transducer and the fluid environmemt.

15. An ultrasonic buffer according to claim 14, wherein the rods are hollow.

16. A buffer according to claim 14, wherein said rods are positioned in edge to edge contact along their length dimension.

17. A buffer according to claim 14, wherein said tightly bundled rods are configured to conduct an effective measurement signal at plural frequencies over a five to one frequency band, conducting each frequency at a different phase velocity.

18. A buffer according to claim 14, wherein said rods are acoustically coupled to a prism having an angled face for launching said measurement signal as a beam directed at an angle in the fluid.

* * * * *